US012714719B2

United States Patent

(12) United States Patent
Meiri et al.
(10) Patent No.: US 12,714,719 B2
(45) Date of Patent: Aug. 25, 2026

(54) CANNABINOIDS, PHARMACEUTICAL COMPOSITIONS COMPRISING SAME AND USES THEREOF

(71) Applicant: TECHNION RESEARCH AND DEVELOPMENT FOUNDATION LIMITED, Haifa (IL)

(72) Inventors: David Meiri, Haifa (IL); Elazar Besser, Haifa (IL); Gil Moshe Lewitus, Haifa (IL); Paula Berman, Haifa (IL)

(73) Assignees: David Meiri, Haifa (IL); Elazar Besser, Haifa (IL); Gil Moshe Lewitus, Haifa (IL); Paula Berman, Haifa (IL)

( * ) Notice: Subject to any disclaimer, the term of this patent is extended or adjusted under 35 U.S.C. 154(b) by 500 days.

(21) Appl. No.: 18/252,715

(22) PCT Filed: Nov. 14, 2021

(86) PCT No.: PCT/IL2021/051352
§ 371 (c)(1),
(2) Date: May 11, 2023

(87) PCT Pub. No.: WO2022/101917
PCT Pub. Date: May 19, 2022

(65) Prior Publication Data
US 2023/0414639 A1 Dec. 28, 2023

Related U.S. Application Data

(60) Provisional application No. 63/113,905, filed on Nov. 15, 2020.

(51) Int. Cl.
*A61K 31/00* (2006.01)
*A61K 36/185* (2006.01)
(Continued)

(52) U.S. Cl.
CPC ........ *A61K 31/658* (2023.05); *A61K 36/3482* (2024.05); *A61P 17/06* (2018.01); *A61P 35/00* (2018.01)

(58) Field of Classification Search
CPC ......... A61K 31/658; A61P 17/06; A61P 35/00
See application file for complete search history.

(56) References Cited

U.S. PATENT DOCUMENTS 4,235,871 A 11/1980 Papahadjopoulos
4,501,728 A 2/1985 Geho
(Continued)

FOREIGN PATENT DOCUMENTS

CN 111084765 A 5/2020
EP 0494665 A1 7/1992
(Continued)

OTHER PUBLICATIONS

Baram et al., (2019) The heterogeneity and complexity of Cannabis extracts as antitumor agents. Oncotarget 10(41): 4091-4106.
(Continued)

*Primary Examiner* — Sarah Pihonak
*Assistant Examiner* — Jackson J Hernandez
(74) *Attorney, Agent, or Firm* — FULLER IP LAW LLC; Rodney J. Fuller

(57) ABSTRACT

The present invention provides a pharmaceutical composition including one or more cannabinoids, and methods of using same, such as for treating NOTCH-related diseases.

11 Claims, 13 Drawing Sheets

(51) Int. Cl.
*A61P 17/06* (2006.01)
*A61P 35/00* (2006.01)

(56) References Cited

U.S. PATENT DOCUMENTS

| | | | |
|---|---|---|---|
| 4,666,828 | A | 5/1987 | Gusella |
| 4,683,202 | A | 7/1987 | Mullis |
| 4,801,531 | A | 1/1989 | Frossard |
| 4,837,028 | A | 6/1989 | Allen |
| 5,019,369 | A | 5/1991 | Presant |
| 5,192,659 | A | 3/1993 | Simons |
| 5,272,057 | A | 12/1993 | Smulson |
| 2006/0074252 | A1 | 4/2006 | Souza |

FOREIGN PATENT DOCUMENTS

| | | | |
|---|---|---|---|
| WO | 03049727 | A1 | 6/2003 |
| WO | 2008144475 | A1 | 11/2008 |
| WO | 2011110866 | A1 | 9/2011 |
| WO | 2013038157 | A1 | 3/2013 |
| WO | 2018154280 | A1 | 8/2018 |
| WO | 2018205038 | A1 | 11/2018 |
| WO | 2020024009 | A1 | 2/2020 |
| WO | 2020024011 | A1 | 2/2020 |
| WO | 2020223510 | A1 | 11/2020 |
| WO | 2020230145 | A1 | 11/2020 |
| WO | 2021151168 | A1 | 8/2021 |

OTHER PUBLICATIONS

Berman et al., (2018) A new ESI-LC/MS approach for comprehensive metabolic profiling of phytocannabinoids in Cannabis. Sci Rep 8(1): 14280.

Borggrefe and Oswald (2009) The Notch signaling pathway: transcriptional regulation at Notch target genes. Cell Mol Life Sci 66(10): 1631-1646.

Buchwald et al., (1980) Long-term, continuous intravenous heparin administration by an implantable infusion pump in ambulatory patients with recurrent venous thrombosis. Surgery 88(4): 507-516.

Gao Bingbing (2016) Cannabidiol Can Provide Neuroprotection in a Mouse Model of Intracerebral Hemorrhage and the Mechanism Research. Published Oct. 15, 2016, Thesis; China Excellent Master's Thesis Database. Anhui Medical University. 43 pages. English abstract and machine translation of pp. 20-21.

Horváth et al., (2019) Methodological refinement of Aldara-induced psoriasiform dermatitis model in mice. Sci Rep 9 (1): 3685.

Langer (1990) New methods of drug delivery. Science 249(4976): 1527-1533.

Punzo et al., (2017) Anti-proliferative, pro-apoptotic and anti-invasive effect of EC/EV system in human osteosarcoma. Oncotarget 8(33): 54459-54471.

Reece and Hulse (2019) Impacts of cannabinoid epigenetics on human development: reflections on Murphy et al. 'cannabinoid exposure and altered DNA methylation in rat and human sperm' epigenetics 2018; 13: 1208-1221. Epigenetics 14(11): 1041-1056.

Sanjana et al., (2014) Improved vectors and genome-wide libraries for CRISPR screening. Nat Methods. Author manuscript; available in PMC Jun. 30, 2015. Published in final edited form as: Nat Methods. Aug. 2014; 11(8): 783-784.

Saudek et al., (1989) A preliminary trial of the programmable implantable medication system for insulin delivery. N Engl J Med 321(9): 574-579.

Sefton (1987) Implantable pumps. Crit Rev Biomed Eng 14(3): 201-240.

Somovilla-Crespo et al., (2018) 92R Monoclonal Antibody Inhibits Human CCR9+ Leukemia Cells Growth in NSG Mice Xenografts. Front Immunol 9: 77.

Van der Fits et al., (2009) Imiquimod-induced psoriasis-like skin inflammation in mice is mediated via the IL-23/IL-17 axis. J Immunol 182(9): 5836-5845.

Wang et al., (2020) Notch-Hes1 Signaling Regulates IL-17A+γδ+T Cell Expression and IL-17A Secretion of Mouse Psoriasis-Like Skin Inflammation. Mediators Inflamm 2020: 8297134.

Treatment with vehicle or CBD:CF1 concentrations in µg/ml

Treatment with vehicle or CBD:CF1 concentrations in μg/ml

CANNABINOIDS, PHARMACEUTICAL COMPOSITIONS COMPRISING SAME AND USES THEREOF

CROSS-REFERENCE TO RELATED APPLICATIONS

This application is the U.S. National Stage of International Patent Application No. PCT/IL2021/051352, filed on Nov. 14, 2021, which claims the benefit of and priority to U.S. Provisional Patent Application No. 63/113,905, filed on Nov. 15, 2020, the contents of each of which are hereby incorporated by reference in their entireties.

FIELD OF INVENTION

The present invention relates to cannabinoid compounds, pharmaceutical compositions comprising same, and methods of use thereof.

BACKGROUND

NOTCH signaling has been found in various diseases, inclusive of cancers, such as breast, prostate and colorectal; as well as in non-cancerous diseases. Targeting NOTCH signaling components has generated much interest for its therapeutic potential. The intracellular domain of the NOTCH protein (NICD) is the active product of NOTCH 1 and is a part of a transcription factor complex regulating the expression of genes, such as MYC and HES1. MYC is an oncogenic transcription factor that controls cell growth and metabolism. Therefore, it seems that the aberrant cell proliferation and increased survival of T-ALLs are partly controlled by the NOTCH 1-MYC. Preventing NOTCH 1 maturation may result in downregulation of the active product NICD and inhibition of its transcription activity. This, in turn, may lead to the downregulation of MYC and HES1 proto-oncogenes. Maturation of NOTCH 1 by S1 furin-like cleavage was shown to be inhibited by CHAC1. Blocking NOTCH maturation through JNK1/c-JUN-CHAC1 pathways and inhibiting the S1 furin-like cleavage of NOTCH, have the potential to affect all types of active mutations in NOTCH and also to affect all four human homologs of NOTCH (NOTCH 1-4).

Previous attempts to target the NOTCH via a related gamma-secretase inhibitor (GSI), have been unsuccessful.

WO 2020/230145 discloses a method for treating a subject afflicted with a NOTCH 1-related disease comprising a step of administering to the subject a composition comprising two or more cannabinoids, selected from: CF1, cannabidiol (CBD) and cannabidivarin (CBDV). Further provided is a pharmaceutical composition comprising CF1, CBD, and CBDV.

There is still a great need for pharmaceutical compositions suitable for treating diseases related to NOTCH genes and their encoded proteins.

SUMMARY

The present invention is directed to pharmaceutical compositions useful in the treatment of NOTCH 2, NOTCH 3, and/or NOTCH 4-related diseases or disorders.

The present invention is based, in part, on the unexpected finding that the phytocannabinoid denoted CF1 is a highly potent anti-cancer agent which induces apoptosis of various cancer cells either alone or in combination with additional cannabinoids such as CBD, CBDV, or both.

According to a first aspect, there is provided a pharmaceutical composition comprising as an active ingredient a cannabinoid referred to as CF1 and a pharmaceutically acceptable carrier, for use in the treatment of a disease related to any one of: NOTCH 2, NOTCH 3, NOTCH 4, and combinations thereof. Each possibility represents a separate embodiment.

According to a second aspect, there is provided a method of treating a subject afflicted with a disease related to any one of: NOTCH2, NOTCH3, NOTCH4, and combinations thereof, the method comprising administering to said subject a therapeutically effective amount of a pharmaceutical composition comprising as an active ingredient a cannabinoid referred to as CF1 and a pharmaceutically acceptable carrier.

According to one embodiment, the disease related to any one of NOTCH 2, NOTCH 3, NOTCH 4, and combinations thereof is selected from the group consisting of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder. Each possibility represents a separate embodiment.

According to another embodiment, the disease related to any one of NOTCH 2, NOTCH 3, NOTCH 4 and combinations thereof is characterized by an abnormal expression level of a NOTCH protein.

According to some embodiments, CF1 constitutes more than 50% by weight of the cannabinoids in the pharmaceutical composition.

According to other embodiments, the pharmaceutical composition comprises CF1 as the sole cannabinoid.

According to certain embodiments, the pharmaceutical composition further comprises at least one additional cannabinoid.

According to various embodiments, the pharmaceutical composition further comprises CBD, CBDV, or both. Each possibility represents a separate embodiment.

According to some embodiments, CF1 and at least one of CBD and CBDV constitute more than 50% by weight of the cannabinoids in the pharmaceutical composition.

According to further embodiments, the pharmaceutical composition comprises CF1, CBD, and CBDV.

According to particular embodiments, CF1, CBD, and CBDV constitute more than 50% by weight of the cannabinoids in the pharmaceutical composition.

According to another aspect, there is provided a pharmaceutical composition comprising cannabinoids, wherein more than 50% by weight of the cannabinoids is CF1.

According to some embodiments, CF1 is a compound having a structure represented by Formula 1:

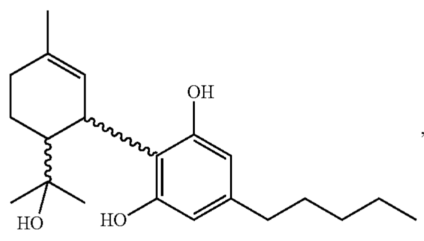 [SMILES: CCCCCc1cc(O)c(C2C=C(C)CCC2C(C)(C)O)c(O)c1], wherein each wavy bond, independently, represents an S-configuration or an R-configuration of a chiral carbon atom.

According to other embodiments, there is provided a pharmaceutical composition comprising CF1 as the sole active ingredient.

According to further embodiments, the pharmaceutical composition further comprises at least one additional cannabinoid.

According to particular embodiments, the pharmaceutical composition further comprises CBD, CBDV, or both. Each possibility represents a separate embodiment.

According to various embodiments, one or more of the cannabinoids in the composition is present as a highly purified extract of *Cannabis.*

According to certain embodiments, one or more of the cannabinoids in the composition is a synthetically produced cannabinoid.

According to another aspect, there is provided a pharmaceutical composition comprising cannabinoids, wherein more than 50% by weight of the cannabinoids is CF1, and a pharmaceutically acceptable carrier, for use in the treatment of a NOTCH-related disease.

According to yet another aspect, there is provided a method for treating a subject afflicted with a NOTCH-related disease, the method comprising administering to the subject a therapeutically effective amount of a pharmaceutical composition comprising cannabinoids, wherein more than 50% by weight of the cannabinoids is CF1.

According to some embodiments, the NOTCH is NOTCH 1, and the NOTCH-related disease is selected from the group consisting of: T cell acute lymphoblastic leukemia (T-ALL), Chronic lymphocytic leukemia (CLL), Melanoma, Cholangiocarcinoma (CCC), Colorectal cancer, Lung adenocarcinoma, Glioblastoma, Renal cell carcinoma, Ovarian cancer, Prostate cancer, Breast cancer, Pancreatic ductal adenocarcinoma (PDAC), Cervical cancer, Head and neck squamous cell carcinomas (HNSCC), Hepatocellular carcinoma (HCC), Medulloblastoma, B cell acute lymphoblastic leukemia (B-ALL), Acute myeloid leukemia (AML), Small cell lung carcinoma (SCLC), Lung squamous cell carcinoma (SqCC), Cutaneous squamous cell carcinoma (SqCC), and Chronic myelomonocytic leukemia (CMML). Each possibility represents a separate embodiment.

According to other embodiments, the disease is selected from the group consisting of: Cutaneous T-cell lymphoma (CTCL) including Mycosis fungoides and Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, B cell malignancy, T cell lymphoma, Pancreatic cancer, Nasopharyngeal carcinoma, Squamous cell carcinoma, Prostatic adenocarcinoma, Non-small-cell lung carcinoma (NSCLC), Infantile myofibromatosis (IM), lateral meningocele syndrome, and desmoid tumor. Each possibility represents a separate embodiment.

According to further embodiments, the disease is selected from the group consisting of: Mycosis fungoides, Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, Nasopharyngeal carcinoma, Infantile myofibromatosis (IM), lateral meningocele syndrome, and desmoid tumor. Each possibility represents a separate embodiment.

According to several embodiments, the disease is selected from the group consisting of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder. Each possibility represents a separate embodiment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 4 shows dose-dependent AlamarBlue® (resazurin) viability assays performed on Molt-4 cells treated with different concentrations of three phytocannabinoids (CBD, CBDV and CF1) at different ratios.

DETAILED DESCRIPTION

Figure 1A:
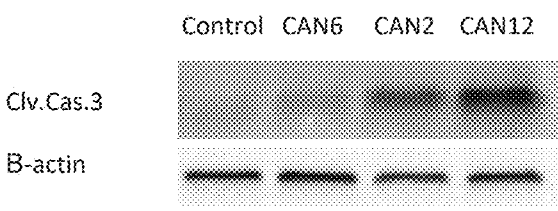
FIGS. 1A-1C show the effects of *Cannabis* extracts on apoptosis induction and NICD levels.

The present invention provides cannabinoid compounds, cannabinoid compositions, plant extracts comprising cannabinoids, and methods of use thereof in treating or ameliorating a disease related to NOTCH signaling, particularly diseases involving abnormal NOTCH signaling.

According to some embodiments, the invention is based, in part, on the surprising findings of specific cannabinoid compositions which possess an apoptotic inducing effect over different types of cancer cells, e.g., tolerant cancer cells, and cancer cells harboring different mutations, including e.g. mutations in NOTCH 4. Accordingly, compositions comprising the cannabinoids are useful in the treatment of various diseases and disorders including, but not limited to, different types of cancers, and other proliferative diseases.

Cannabinoids and Compositions

In some embodiments, the compositions disclosed herein comprise a cannabinoid referred to as CF1. According to some embodiments, CF1 is a compound having a structure represented by Formula 1:

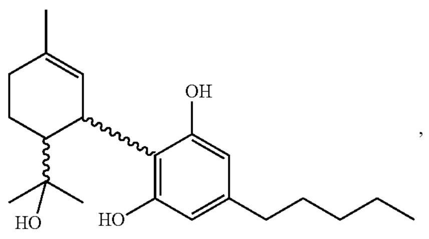 [SMILES: CCCCCc1cc(O)c(C2C=C(C)CCC2C(C)(C)O)c(O)c1]

, wherein each wavy bond, independently, represents an S-configuration or an R-configuration of a chiral carbon atom. In some embodiments, CF1 is a phytocannabinoid.

According to some embodiments, CF1 is a compound having a deprotonated accurate mass of 331.227 Da, and a retention time of 7.14 min. In some embodiments, CF1 is characterized by an accurate mass of 332.2 Da and by the following chemical composition $C_{21}H_{32}O_3$. In some embodiments, CF1 is characterized by a retention time of 7.14 minutes when analyzed by UHPLC, under conditions described in WO 2020/230145 (the contents of which are incorporated by reference herein in their entirety). In some embodiments, CF1 is a single isomer. In some embodiments, CF1 is a mixture of diastereomers (i.e. RS, RR, SS, SR). Each possibility represents a separate embodiment.

In some embodiments, CF1 is 1,3-benzenediol,2-[(1R, 6R)-6-(1-hydroxy-1-methylethyl)-3-methyl-2cyclohexen-1-yl]-5-pentyl.

In some embodiments, the cannabinoid is a phytocannabinoid. As used herein, a "phytocannabinoid" is a cannabinoid that originates in nature from the *Cannabis* plant. Examples of cannabinoids include, but are not limited to, CF1, cannabidiol (CBD), cannabidivarin (CBDV), (-)-$\Delta^9$-trans-tetrahydrocannabinol ($\Delta^9$-THC), (-)-$\Delta^9$-trans-tetrahydrocannabinolic acid ($\Delta^9$-THCA), (-)-$\Delta^9$-trans-tetrahydrocannabivarin ($\Delta^9$-THCV), (-)-$\Delta^9$-trans-tetrahydrocannabivarinic acid ($\Delta^9$-THCVA), cannabinol (CBN), cannabivarin (CBNV), cannabicyclol (CBL), cannabigerol (CBG), cannabigerovarin (CBGV), cannabidiolic acid (CBDA), cannabichromene (CBC), cannabichromenic acid (CBCA) and any derivative thereof. Each possibility represents a separate embodiment.

In some embodiments, the present invention is directed to a composition derived from a plant extract. In some embodiments, a plant extract of the invention is derived from a plant comprising cannabinoids. In some embodiments, the plant extract of the invention is derived from a *Cannabis* plant. In some embodiments, the plant extract is derived from a specific species of the *Cannabis* genus. In some embodiments, the *Cannabis* species is selected from *Cannabis sativa, Cannabis indica, Cannabis ruderalis*, and a mixture or combination thereof. Each possibility represents a separate embodiment.

In some embodiments, the invention relates to a composition comprising CF1 as an active ingredient. In some embodiments, the invention relates to a composition comprising CF1 as the active ingredient. In some embodiments, the invention relates to a composition comprising CF1 as the sole cannabinoid in said composition. In some embodiments, the invention relates to a composition consisting essentially of CF1. In some embodiments, the invention relates to a composition comprising CF1 in an amount which is more than 50% by weight of the total cannabinoid content in the composition. In some embodiments, CF1 constitutes more than 50% by weight of the cannabinoids of the composition. In some embodiments, more than 50% by weight of the cannabinoids in the composition is CF1.

Exemplary weight percentages of CF1 include, but are not limited to, 51%, 55%, 60%, 65%, 70%, 75%, 80%, 85%, 90%, 95%, 99% or even 100% of the total cannabinoid content in the composition. Each possibility represents a separate embodiment.

In some embodiments, the composition further comprises one or more additional cannabinoids.

According to some embodiments, the invention relates to a composition comprising a plurality of cannabinoids. In some embodiments, the composition comprises CF1 and at least one of CBD and CBDV. In some embodiments, the composition comprises a plurality of cannabinoids selected from: CF1, CBD, and CBDV. In some embodiments, the composition comprises CF1. In some embodiments, the composition comprises CBD. In some embodiments, the composition comprises CBDV.

In some embodiments, the composition comprises CF1 and CBD. In some embodiments, the composition comprises CF1 and CBDV. In some embodiments, the composition comprises CBD and CBDV. In some embodiments, the composition comprises CF1, CBD, and CBDV.

In some embodiments, the composition is a pharmaceutical composition.

In some embodiments, at least 0.1%, 0.5%, 1%, 2%, 3%, 5%, 10%, 20%, 30%, 40%, 50%, 60%, 70%, 80%, 85%, 90%, 95%, or 99% and up to 100% by weight of the cannabinoid content in the composition is CF1, or any value and range therebetween. Each possibility represents a separate embodiment of the invention. In some embodiments, the composition comprises at most 0.5%, 1%, 5%,10%, 25%, 40%, 50%, 60%, 70%, 80%, 90%, 95% or 99% by weight CF1, or any value and range therebetween. Each possibility represents a separate embodiment of the invention.

In some embodiments, at least 1%, 5%, 10%, 20%, 30%, 40%, 50%, 60%, 70%, 80%, 85%, 90%, 95%, or 99% and up to 100% by weight of the cannabinoid content in the composition is CBD, or any value and range therebetween. Each possibility represents a separate embodiment of the invention. In some embodiments, the composition comprises at most 1%, 5%, 10%, 20%, 30%, 40%, 50%, 60%, 70%, 80%, 90%, 95% or 99% by weight CBD, or any value and range therebetween. Each possibility represents a separate embodiment of the invention.

In some embodiments, at least 1%, 5%, 10%, 20%, 30%, 40%, 50%, 60%, 70%, 80%, 85%, 90%, 95%, or 99% and up to 100% by weight of the cannabinoid content in the composition is CBDV, or any value and range therebetween. Each possibility represents a separate embodiment of the invention. In some embodiments, the composition comprises at most 1%, 5%, 10%, 20%, 30%, 40%, 50%, 60%, 70%, 80%, 90%, 95% or 99% by weight CBDV, or any value and range therebetween. Each possibility represents a separate embodiment of the invention.

In some embodiments, CF1, CBD, and CBDV combined, comprise at least 45%, 50%, 60%, 70%, 80%, 85%, 90%, 95%, 97%, or 99% and up to 100% by weight, of the total cannabinoids in the composition, or any value and range therebetween. Each possibility represents a separate embodiment of the invention. In some embodiments, CF1, CBD, and CBDV combined, comprise at least 45-80%, 50-75%, 60-95%, 70-99%, 80-100%, 50-85%, 60-90%, 68-97%, or 55-99% by weight, of the total cannabinoids in the composition. Each possibility represents a separate embodiment of the invention.

In some embodiments, CF1, CBD, CBDV, or any combination thereof, constitutes more than 50% by weight of the cannabinoids in the composition.

In some embodiments, the composition comprises a w/w ratio of (i) CF1 and (ii) at least one of CBD, CBDV, or any combination thereof, selected from 1,000:1 to 1:1,000, 100:1 to 1:1,000; 10:1 to 1:500; 10:1 to 800:1; 10:1 to 1:500; 5:1 to 1:300; 4:1 to 1:200; 3:1 to 1:100; 2:1 to 1:50; 1:1 to 1:20; and 1:1 to 1:15, wherein each possibility represents a separate embodiment of the invention.

In some embodiments, the composition comprises a w/w ratio of (i) CF1 and (ii) CBD, selected from 1,000:1 to 1:1,000, 100:1 to 1:1,000; 10:1 to 1:500; 10:1 to 800:1; 10:1 to 1:500; 5:1 to 1:300; 4:1 to 1:200; 3:1 to 1:100; 2:1 to 1:50; 1:1 to 1:20; and 1:1 to 1:15, wherein each possibility represents a separate embodiment of the invention.

In some embodiments, the composition comprises a w/w ratio of (i) CF1 and (ii) CBDV, selected from 1,000:1 to 1:1,000, 100:1 to 1:1,000; 10:1 to 1:500; 10:1 to 800:1; 10:1 to 1:500; 5:1 to 1:300; 4:1 to 1:200; 3:1 to 1:100; 2:1 to 1:50; 1:1 to 1:20; and 1:1 to 1:15, wherein each possibility represents a separate embodiment of the invention.

In some embodiments, the composition comprises a w/w ratio of (i) CF1 and (ii) a combination of CBD and CBDV, selected from 1,000:1 to 1:1,000, 100:1 to 1:1,000; 10:1 to 1:500; 10:1 to 800:1; 10:1 to 1:500; 5:1 to 1:300; 4:1 to 1:200; 3:1 to 1:100; 2:1 to 1:50; 1:1 to 1:20; and 1:1 to 1:15, wherein each possibility represents a separate embodiment of the invention.

In some embodiments, a unit dose of the pharmaceutical composition comprises cannabinoids in an amount ranging from 0.01 ng to 5,000 mg including any value and range therebetween. For example, a unit dose of the pharmaceutical composition comprises cannabinoids in an amount ranging from 0.01 ng to 100 ng, 0.1 ng to 10 ng, 1 ng to 1,000 ng, 0.1 μg to 10 μg, 1 μg to 1,000 μg, 0.5 μg to 250 μg, 1 ng to 300 ng, 0.5 ng to 1 μg, 0.01 mg to 100 mg, 0.05 mg to 40 mg, 0.08 mg to 15 mg, 0.1 mg to 10 mg, 0.2 mg to 20 mg, 0.5 mg to 50 mg, 0.5 mg to 100 mg, 1 mg to 200 mg, or 1 mg to 500 mg. Each possibility represents a separate embodiment of the invention.

In some embodiments, a unit dose of the pharmaceutical composition comprises CF1 in an amount ranging from 0.01 ng to 100 ng, 0.1 ng to 10 ng, 1 ng to 1,000 ng, 0.1 μg to 10 μg, 1 μg to 1,000 μg, 0.5 μg to 250 μg, 1 ng to 300 ng, or 0.5 ng to 1 μg. Each possibility represents a separate embodiment of the invention.

In some embodiments, a unit dose of the composition comprises CF1 in an amount ranging from 0.01 ng to 100 ng, 0.05 ng to 40 ng, 0.08 ng to 15 ng, 0.1 ng to 10 ng, 0.2 ng to 10 ng, 0.3 ng to 10 ng, 0.5 ng to 10 ng, 0.9 ng to 20 ng, or 1 ng to 50 ng. Each possibility represents a separate embodiment of the invention. In other embodiments, a unit dose of the composition comprises CF1 in an amount ranging from 0.01 μg to 100 μg, 0.05 μg to 40 μg, 0.08 μg to 15 μg, 0.1 μg to 10 μg, 0.2 μg to 10 μg, 0.3 μg to 10 μg, 0.5 μg to 10 μg, 0.9 μg to 20 μg, or 1 μg to 50 μg. Each possibility represents a separate embodiment of the invention. In yet other embodiments, a unit dose of the composition comprises CF1 in an amount ranging from 0.01 mg to 100 mg, 0.05 mg to 40 mg, 0.08 mg to 15 mg, 0.1 mg to 10 mg, 0.2 mg to 10 mg, 0.3 mg to 10 mg, 0.5 mg to 10 mg, 0.9 mg to 20 mg, or 1 mg to 50 mg. Each possibility represents a separate embodiment of the invention. In additional embodiments, the composition comprises CF1 in an amount selected from 1 to 5,000 mg, 1 to 1,000 mg, 1 to 500 mg, 1 to 100 mg, 1 to 10 mg, 100 to 1,000 mg, 10 to 100 mg, 0.1 to 1 mg, and 0.01 to 0.1 mg. Each possibility represents a separate embodiment of the invention.

In one embodiment, the composition comprises CBD in an amount selected from 1 to 5,000 mg, 1 to 1,000 mg, 1 to 500 mg, 1 to 100 mg, 1 to 10 mg, 100 to 1,000 mg, 10 to 100 mg, 0.1 to 1 mg, and 0.01 to 0.1 mg. Each possibility represents a separate embodiment of the invention.

In one embodiment, the composition comprises CBDV in an amount selected from 1 to 5,000 mg, 1 to 1,000 mg, 1 to 500 mg, 1 to 100 mg, 1 to 10 mg, 100 to 1,000 mg, 10 to 100 mg, 0.1 to 1 mg, and 0.01 to 0.1 mg. Each possibility represents a separate embodiment of the invention.

In some embodiments, the cannabinoid is not a psychoactive cannabinoid. In some embodiments, the composition does not comprise a psychoactive cannabinoid.

According to some embodiments, the composition of the invention comprises CF1, CBD, and CBDV and further comprises at least one additional cannabinoid selected from: CBGA, CBG, CBG-C4, CBGV, CBGM, SesquiCBG, THC (including $\Delta^8$ THC, and/or $\Delta^9$ THC), THCA, THCV (including $\Delta^9$ THCV), THCVA (including $\Delta^9$ THCVA), CBDA, CBDA-C4, CBD-C4, CBDVA, CBDO, CBDM, CBCA, CBC, CBC-C4, CBCVA, CBCMA, CBCV, CBCO, CBN, CBNV, OH-CBN, OH-CBNA, CBEA, CBE, CBEV, CBEVA, CBDVA, CBNDA, CBND, CBL, CBT-1, CBTV-1, CBT-3, and CBT-2. Each possibility represents a separate embodiment of the invention.

According to some embodiments, the composition comprises CF1, CDB, CBDV, and further comprises a plurality of additional cannabinoids selected from: CBGA, CBG, CBG-C4, CBGV, CBGM, SesquiCBG, THC (including $\Delta^8$ THC, and/or $\Delta^9$ THC), THCA, THCV (such as $\Delta^9$ THCV), THCVA (including $\Delta^9$ THCVA), CBDA, CBDA-C4, CBD-C4, CBDVA, CBDO, CBDM, CBCA, CBC, CBC-C4, CBCVA, CBCMA, CBCV, CBCO, CBN, CBNV, OH-CBN, OH-CBNA, CBEA, CBE, CBEV, CBEVA, CBDVA, CBNDA, CBND, CBL, CBT-1, CBTV-1, CBT-3, and CBT-2. Each possibility represents a separate embodiment of the invention.

In some embodiments, THC is or comprises $\Delta^8$-THC. In some embodiments, THC is or comprises $\Delta^9$-THC. In some embodiments, THC is or comprises $\Delta^8$-THC and $\Delta^9$-THC.

In some embodiments, THCV is or comprises $\Delta^9$-THCV.

As used herein, the term "a plurality of cannabinoids" refers to two or more cannabinoids, e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, and at least 30, or any value and range therebetween. Each possibility represents a separate embodiment of the invention. In some embodiments, the plurality of cannabinoids of the composition are those having a relative amount of at least 2%, at least 1.5%, at least 1%, at least 0.4%, at least 0.3%, at least 0.2%, at least 0.1%, or any value and range therebetween in a *Cannabis* extract. Each possibility represents a separate embodiment of the invention.

According to some embodiments, the composition of the invention comprises CF1, CBD, CBDV, and at least one additional cannabinoid selected from: CBC, THC, CBDA, CBG, CBE, CBCV, CBD-C4, THCV, CBN, and CBT-1. Each possibility represents a separate embodiment. According to some embodiments, the composition of the invention comprises CF1, CBD, CBDV, CBC, THC, CBDA, CBG, CBE, CBCV, CBD-C4, THCV, CBN, and CBT-1.

In some embodiments, the composition of the invention comprises at least 0.01%, 0.1%, 0.5%, 1%, 5%, 10%, 20%, 30%, 40%, 50%, 60%, 70%, 80%, 90%, 95%, or 99% by weight cannabinoids, or any value and range therebetween. Each possibility represents a separate embodiment of the invention. In some embodiments, the plant extract of the invention comprises at most 0.01%, 0.1%, 0.5%, 1%, 5%, 10%, 20%, 30%, 40%, 50%, 60%, 70%, 80%, 90%, 95%, 99% or 100% by weight cannabinoids, or any value and range therebetween. Each possibility represents a separate embodiment of the invention. In some embodiments, the composition comprises at least 0.001%, 0.01%, 0.1%, 1%, 5%, 10%, 20%, 30%, 40%, 50%, 60%, 70%, 80%, 90%, 95%, or 99% by weight CF1, or any value and range therebetween. Each possibility represents a separate embodiment of the invention. In some embodiments, the composition comprises at most 0.1%, 0.5%, 1%, 5%, 10%, 20%, 30%, 40%, 50%, 60%, 70%, 80%, 90%, 95%, or 99% by weight CF1, or any value and range therebetween. Each possibility represents a separate embodiment of the invention. In some embodiments, the composition comprises at least 0.001%, 0.01%, 0.1%, 1%, 5%, 10%, 20%, 30%, 40%, 50%, 60%, 70%, 80%, 90%, 95%, or 99% by weight CBD, or any value and range therebetween. Each possibility represents a separate embodiment of the invention. In some embodiments, the composition comprises at most 0.1%, 0.5%, 1%, 5%, 10%, 20%, 30%, 40%, 50%, 60%, 70%, 80%, 90%, 95%, or 99% by weight CBD, or any value and range therebetween. Each possibility represents a separate embodiment of the invention. In some embodiments, the composition comprises at least 0.001%, 0.01%, 0.1%, 1%, 5%, 10%, 20%, 30%, 40%, 50%, 60%, 70%, 80%, 90%, 95%, or 99% by weight CBDV, or any value and range therebetween. Each possibility represents a separate embodiment of the invention. In some embodiments, the composition comprises at most 0.1%, 0.5%, 1%, 5%, 10%, 20%, 30%, 40%, 50%, 60%, 70%, 80%, 90%, 95%, or 99% by weight CBDV, or any value and range therebetween. Each possibility represents a separate embodiment of the invention.

The term "consisting essentially of" denotes that a given compound or substance constitutes the vast majority of the active ingredient's portion or fraction of the composition.

In some embodiments, consisting essentially of means that CF1 constitutes at least 95%, at least 98%, at least 99%, or at least 99.9% by weight, of the active ingredient(s) of the composition, or any value and range therebetween. Each possibility represents a separate embodiment of the invention.

In some embodiments, consisting essentially of means that CF1 constitutes at least 95%, at least 98%, at least 99%, or at least 99.9% by weight, of the total cannabinoids content of the composition.

In some embodiments, the composition comprises or consists of a plant extract.

As used herein, the term "extract" comprises the whole extract, a fraction thereof, a portion thereof, an isolated compound therefrom, or any combination thereof.

In some embodiments, the extract is derived from a plant material.

In some embodiments, the plant material is first dried and then extracted. In some embodiments, the plant material is air-dried. In some embodiments, the plant material is further heat treated (e.g., hot-drying) and then extracted.

As used herein, treatment before extraction comprises, for example, freezing, drying, lyophilizing, or any combination thereof. Each possibility represents a separate embodiment.

In some embodiments, the plant material is further processed prior to the extraction procedure in order to facilitate the extraction procedure. In some embodiments, processing methods prior to extraction include, but are not limited to, crushing, slicing, or shredding, such as by using a grinder or other devices to fragment the plant parts into small pieces or powder.

In some embodiments, the cannabinoids undergo decarboxylation prior to or after the extraction procedure.

In some embodiments, the extraction comprises at least one of organic solvent extraction, carbon dioxide (dry ice) extraction, supercritical and subcritical carbon dioxide extraction, hydrocarbon extraction, rosin press, and a combination thereof. Each possibility represents a separate embodiment. In some embodiments, the extraction is a solvent-based extraction. In some embodiments, the solvent is a polar solvent. As used herein, a polar solvent includes, but is not limited to, ethanol and isopropyl. In some embodiments, the solvent is a non-polar solvent. In some embodiments, the extraction is a solvent-free extraction.

In some embodiments, the *Cannabis*-derived substance used in the compositions and methods as described herein includes CF1. In one embodiment, the composition described herein comprises purified or substantially purified (e.g., greater than 80% w/w, 85% w/w, 90% w/w, 95% w/w, or 97% w/w) CF1. In some embodiments of the methods described herein, purified or substantially purified (e.g., greater than 80% w/w, 85% w/w, 90% w/w, 95% w/w, or 97% w/w) CF1 is administered to a subject suffering from a disease or a condition as described herein.

In one embodiment, the *Cannabis*-derived substance used in the compositions and methods as described herein includes CBD, or a functional variant thereof. In one embodiment, the composition described herein comprises purified or substantially purified (e.g., greater than 80% w/w, 85% w/w, 90% w/w, 95% w/w, or 97% w/w) CBD. In some embodiments of the methods described herein, purified or substantially purified (e.g., greater than 80% w/w, 85% w/w, 90% w/w, 95% w/w, or 97% w/w) CBD, or a functional variant thereof, is administered to a subject suffering from a disease or a condition as described herein.

In one embodiment, the *Cannabis*-derived substance used in the compositions and methods as described herein includes CBDV, or a functional variant thereof. In one embodiment, the composition described herein comprises purified or substantially purified (e.g., greater than 80% w/w, 85% w/w, 90% w/w, 95% w/w, or 97% w/w) CBDV. In some embodiments of the methods described herein, purified or substantially purified (e.g., greater than 80% w/w, 85% w/w, 90% w/w, 95% w/w, or 97% w/w) CBDV, or a functional variant thereof, is administered to a subject suffering from a disease or a condition as described herein.

As used herein, the term "synthetic cannabinoids" refers to compounds that have a cannabinoid or cannabinoid-like structure and are manufactured using chemical means rather than by the plant.

According to some embodiments, there is provided a pharmaceutical composition comprising CF1 and optionally CBD, CBDV, as well as additional cannabinoids disclosed herein, and a pharmaceutically acceptable carrier.

As used herein, the terms "carrier", "excipient", or "adjuvant" refer to any component of a pharmaceutical composition that is not the active agent. As used herein, the term "pharmaceutically acceptable carrier" refers to non-toxic, inert solid, semi-solid or liquid filler, diluent, encapsulating material, formulation auxiliary of any type, or simply a sterile aqueous medium, such as saline. Each possibility represents a separate embodiment. Some non-limiting examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose, hydroxypropyl cellulose, and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents and pH adjusting agents such as magnesium hydroxide, sodium hydroxide, potassium hydroxide, and aluminum hydroxide; alginic acid; pyrogen-free water; isotonic saline, Ringer's solution; ethyl alcohol and phosphate buffer solutions, as well as other non-toxic compatible substances used in pharmaceutical formulations. Each possibility represents a separate embodiment.

Some additional non-limiting examples of substances which can serve as carriers herein include stearic acid, magnesium stearate, calcium sulfate, vegetable oils, polyols, alginic acid, pyrogen-free water, isotonic saline, phosphate buffer solutions, cocoa butter (suppository base), emulsifier (e.g. carbomer, sodium lauryl sulfate) and the like. Each possibility represents a separate embodiment. Wetting agents and lubricants, as well as coloring agents, flavoring agents, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, the contents of all of which are hereby incorporated by reference in their entirety.

Examples of pharmaceutically acceptable excipients, carriers and diluents useful in the present compositions include distilled water, physiological saline, Ringer's solution, dextrose solution, Hank's solution, and DMSO. Each possibility represents a separate embodiment. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, $21^{st}$ Ed., Lippincott Williams & Wilkins, Philadelphia, Pa., (2005), each of which is incorporated by reference herein in its entirety.

The presently described compositions may also be contained in artificially created structures such as liposomes, ISCOMS, slow-releasing particles, and other vehicles. Each possibility represents a separate embodiment. Liposomes include emulsions, foams, micelles, insoluble monolayers, liquid crystals, phospholipid dispersions, lamellar layers and the like. Each possibility represents a separate embodiment. Liposomes are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, (1999), John Wiley & Sons, Inc., New York, and in U.S. Pat. Nos. 4,235,871; 4,501,728; 4,837,028; and 5,019,369.

The carrier may comprise, in total, from about 0.1% to about 99.99999% by weight of the pharmaceutical compositions presented herein.

A pharmaceutical composition may take any physical form necessary for proper administration. The composition comprising one or more cannabinoid compounds can be administered in any suitable form including, but not limited to, a liquid form, a gel form, a semi-liquid (e.g., a liquid, such as a viscous liquid, containing some solid) form, a semi-solid (a solid containing some liquid) form, or a solid form. Each possibility represents a separate embodiment. Compositions can be provided in, for example, a tablet form, a capsule form, a liquid form, a food form, a chewable form, a non-chewable form, a transbuccal form, a sublingual form, a slow-release form, a non-slow-release form, a sustained release form, or a non-sustained-release form. Each possibility represents a separate embodiment.

A pharmaceutically-acceptable carrier suitable for the preparations of unit dosage forms of a composition as described herein for peroral administration is well-known in the art.

In some embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), stabilizers (e.g. oils, polyethylene glycols), viscosity increasing agents (e.g. carbomer, colloidal silicon dioxide, ethyl cellulose, guar gum), lubricants (e.g. stearic acid, magnesium stearate), flow-aids (e.g. colloidal silicon dioxide), plasticizers (e.g. diethyl phthalate, triethyl citrate), polymers (e.g., poloxamers or poloxamines), and/or coatings and film forming agents (e.g. ethyl cellulose, acrylates, polymethacrylates). Each possibility represents a separate embodiment.

Methods of Use

According to some embodiments, there is provided a method for treating a subject afflicted with a NOTCH-related disease, comprising administering to the subject a therapeutically effective amount of a pharmaceutical composition comprising cannabinoids, wherein more than 50%, more than 60%, more than 70%, more than 80%, more than 90%, more than 95%, more than 97%, more than 99%, or 100%, by weight of the cannabinoids is CF1, or any value and range therebetween. Each possibility represents a separate embodiment of the invention.

According to some embodiments, there is provided a method for treating a subject afflicted with a NOTCH 1-related disease, comprising administering to the subject a therapeutically effective amount of a pharmaceutical composition comprising cannabinoids, wherein more than 50%, more than 60%, more than 70%, more than 80%, more than 90%, more than 95%, more than 97%, more than 99%, or 100%, by weight of the cannabinoids is CF1, or any value and range therebetween. Each possibility represents a separate embodiment of the invention.

According to some embodiments, there is provided a method for treating a subject afflicted with a disease selected from T cell acute lymphoblastic leukemia (T-ALL), Chronic lymphocytic leukemia (CLL), Melanoma, Cholangiocarcinoma (CCC), Colorectal cancer, Lung adenocarcinoma, Glioblastoma, Renal cell carcinoma, Ovarian cancer, Prostate cancer, Breast cancer, Pancreatic ductal adenocarcinoma (PDAC), Cervical cancer, Head and neck squamous cell carcinomas (HNSCC), Hepatocellular carcinoma (HCC), Medulloblastoma, B cell acute lymphoblastic leukemia (B-ALL), Acute myeloid leukemia (AML), Small cell lung carcinoma (SCLC), Lung squamous cell carcinoma (SqCC), Cutaneous squamous cell carcinoma (SqCC), and Chronic myelomonocytic leukemia (CMML), comprising administering to the subject a therapeutically effective amount of a pharmaceutical composition comprising cannabinoids, wherein more than 50%, more than 60%, more than 70%, more than 80%, more than 90%, more than 95%, more than 97%, more than 99%, or 100%, by weight of the cannabinoids is CF1, or any value and range therebetween. Each possibility represents a separate embodiment of the invention.

In some embodiments, the pharmaceutical composition comprising cannabinoids, comprises CF1 in an amount of 50.5-100%, 60-99%, 70-95%, 80-97%, 90-96%, 95-99%, or 97-100%, by weight of the cannabinoids. Each possibility represents a separate embodiment of the invention.

According to some embodiments, there is provided a method for treating a subject afflicted with a NOTCH-related disease, comprising administering to the subject a therapeutically effective amount of a composition comprising CF1 as the active agent, thereby treating a subject afflicted with a NOTCH-related disease. In some embodiments, the disease is related to NOTCH 2, NOTCH 3, NOTCH 4, or a combination thereof. Each possibility represents a separate embodiment.

According to some embodiments, there is provided a method for treating a subject afflicted with a disease selected from: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts or leukoencephalopathy (CADASIL) disorder, the method comprising administering to the subject a therapeutically effective amount of a pharmaceutical composition comprising CF1. Each possibility represents a separate embodiment.

According to some embodiments, there is provided a method for treating a subject afflicted with a disease selected from: Cutaneous T-cell lymphoma (CTCL) including Mycosis fungoides and Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, B cell malignancy, T cell lymphoma, Pancreatic cancer, Nasopharyngeal carcinoma, Squamous cell carcinoma, Prostatic adenocarcinoma, Non-small-cell lung carcinoma (NSCLC), Infantile myofibromatosis (IM), lateral meningocele syndrome, and desmoid tumor, the method comprising administering to the subject a therapeutically effective amount of a pharmaceutical composition comprising CF1. Each possibility represents a separate embodiment.

According to some embodiments, there is provided a method for treating a subject afflicted with a disease selected from: Mycosis fungoides, Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, Nasopharyngeal carcinoma, Infantile myofibromatosis (IM), lateral meningocele syndrome, and desmoid tumor, the method comprising administering to the subject a therapeutically effective amount of a pharmaceutical composition comprising CF1. Each possibility represents a separate embodiment According to some embodiments, there is provided the use of CF1 for the preparation of a medicament for treating a disease related to NOTCH 2, NOTCH 3, NOTCH 4, or a combination thereof. Each possibility represents a separate embodiment.

According to some embodiments, there is provided the use of CF1 for the preparation of a medicament for treating a disease selected from: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts or leukoencephalopathy (CADASIL) disorder. Each possibility represents a separate embodiment.

According to some embodiments, there is provided the use of CF1 for the preparation of a medicament for treating a disease selected from: Cutaneous T-cell lymphoma (CTCL) including Mycosis fungoides and Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, B cell malignancy, T cell lymphoma, Pancreatic cancer, Nasopharyngeal carcinoma, Squamous cell carcinoma, Prostatic adenocarcinoma, Non-small-cell lung carcinoma (NSCLC), Infantile myofibromatosis (IM), lateral meningocele syndrome, and desmoid tumor. Each possibility represents a separate embodiment.

According to some embodiments, there is provided the use of CF1 for the preparation of a medicament for treating a disease selected from: Mycosis fungoides, Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, Nasopharyngeal carcinoma, Infantile myofibromatosis (IM), lateral meningocele syndrome, and desmoid tumor. Each possibility represents a separate embodiment.

According to some embodiments, the methods of use disclosed herein comprise treating or preventing a NOTCH-related disease.

In some embodiments, the methods of use disclosed herein comprise ameliorating at least one symptom in a subject afflicted with a NOTCH-related disease.

In some embodiments, the herein disclosed cannabinoids and compositions comprising same are used as anti-NOTCH-related disease agents.

In some embodiments, a NOTCH gene or protein is a human NOTCH gene or protein.

In some embodiments, a NOTCH comprises: NOTCH 1, NOTCH 2, NOTCH 3, and NOTCH 4. Each possibility represents a separate embodiment.

In some embodiments, the disease is related to any one of: NOTCH 1, NOTCH 2, NOTCH 3, NOTCH 4, and/or any combination thereof. Each possibility represents a separate embodiment.

In some embodiments, the disease is related to any one of: NOTCH 2, NOTCH 3, NOTCH 4, and/or any combination thereof. Each possibility represents a separate embodiment.

In some embodiments, the methods of use disclosed herein further comprise a step of determining the expression level of a NOTCH protein or a gene encoding same, of the subject.

In some embodiments, the methods of use disclosed herein further comprise a step of determining the expression level of a gene regulated by NOTCH of the subject.

In some embodiments, the methods of use disclosed herein further comprise a step of determining the presence of a mutation in a NOTCH gene of the subject.

In some embodiments, the methods of use disclosed herein further comprise a step of determining the presence of a mutation in a NOTCH-associated gene of the subject.

In some embodiments, the determining step is performed in the subject or in a sample derived or obtained from the subject. In some embodiments, the sample comprises any bodily fluid, cell, tissue, biopsy, organ, or a combination thereof, derived or obtained from the subject. Each possibility represents a separate embodiment. In some embodiments, the determining step is performed in vivo, ex vivo, or in vitro. Each possibility represents a separate embodiment.

As used herein, the terms "administering", "administration", and the like refer to any method which affords the delivery of a composition containing an active agent to a subject in such a manner so as to provide a therapeutic effect. Suitable routes of administration include, but are not limited to, oral, dermal, transdermal, parenteral, subcutaneous, intravenous, intramuscular, or intraperitoneal. Each possibility represents a separate embodiment. In some embodiments, the administration is systemic. In some embodiments, the administration is local, for example to the site of inflammation. Administering the composition to a specific site in the subject may be performed with any method known in the art. This may include, for example administration using an applicator, in the form of a gel or cream, as well as on a scaffold, wrap or bandage. Each possibility represents a separate embodiment.

As used herein, the terms "treatment" or "treating" of a disease, disorder or condition encompasses alleviation of at least one symptom thereof, a reduction in the severity thereof, or inhibition of the progression thereof. Treatment does not necessarily mean that the disease, disorder or condition is totally cured. To be an effective treatment, a useful composition herein needs only to reduce the severity of a disease, disorder, or condition, reduce the severity of symptoms associated therewith, or provide improvement to a patient or subject's quality of life. In some embodiments, alleviated symptoms of the disease, disorder or condition include reduced cell viability, induced cell apoptosis, inhibited cell proliferation, reduced or increased protein expression. In some embodiments, reduced or increased protein expression relates to a NOTCH protein, e.g., NOTCH and/or a protein encoded by a NOTCH gene, e.g., NOTCH-encoding gene.

As used herein, the term "prevention" of a disease, disorder, or condition encompasses the delay, suppression, or inhibition of the onset of a disease, disorder, or condition. As used in accordance with the presently described subject matter, the term "prevention" relates to a process of prophylaxis in which a subject is exposed to the presently described compositions prior to the induction or the onset of the disease/disorder. This could be done where an individual has a genetic pedigree indicating a predisposition toward the occurrence of the disease/disorder to be prevented. For example, this might be applicable for an individual whose ancestors show a predisposition toward certain types of, for example, inflammatory or proliferative disorders. The term "suppression" is used to describe a condition wherein the disease/disorder process has already begun but obvious symptoms of the condition have yet to be realized. Thus, while an individual is already afflicted with the disease/disorder, no apparent symptoms of the disease/disorder have been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, "treating" comprises ameliorating and/or preventing.

As used herein, the term NOTCH-related disease, refers to any disease, condition, disorder, pathology, or any combination thereof, in which a NOTCH gene or a protein encoded therefrom is involved. This term also refers to diseases in which the pathogenesis, pathophysiology, or both are induced, initiated, propagated, or any combination or equivalent thereof by a NOTCH gene or a protein.

In some embodiments, a NOTCH-related disease comprises a proliferative disease.

As used herein, the term "proliferative disease" comprises a disease or disorder characterized by an increase of cell proliferation. In some embodiments, the cell proliferation is an abnormal cell proliferation. In some embodiments, the cell proliferation is an unregulated cell proliferation.

In some embodiments, a cell proliferation disease comprises or is cancer.

In some embodiments, a NOTCH-related disease comprises or is cancer.

As used herein, "cancer" encompasses diseases associated with abnormal cell proliferation. Non-limiting types of cancer include carcinoma, sarcoma, lymphoma, leukemia, blastoma and germ cells tumors. In one embodiment, carcinoma refers to tumors derived from epithelial cells including, but not limited to, breast cancer, prostate cancer melanoma, lung cancer, pancreas cancer, bile duct cancer, colorectal cancer, lung cancer, non-small cell lung carcinoma (NSCLC), skin cancer (melanoma) and colon cancer. Each possibility represents a separate embodiment. In one embodiment, sarcoma refers of tumors derived from mesenchymal cells including, but not limited to, sarcoma botryoides, chondrosarcoma, Ewing's sarcoma, malignant hemangioendothelioma, malignant schwannoma, osteosarcoma and soft tissue sarcomas. Each possibility represents a separate embodiment. In one embodiment, lymphoma refers to tumors derived from hematopoietic cells that leave the bone marrow and tend to mature in the lymph nodes including, but not limited to, Hodgkin lymphoma, non-Hodgkin lymphoma, Cutaneous T-cell lymphoma (CTCL), multiple myeloma and immunoproliferative diseases. Each possibility represents a separate embodiment. In one embodiment, leukemia refers to tumors derived from hematopoietic cells that leave the bone marrow and tend to mature in the blood including, but not limited to, T-cell acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. Each possibility represents a separate embodiment. In one embodiment, blastoma refers to tumors derived from immature precursor cells or embryonic tissue including, but not limited to, hepatoblastoma, medulloblastoma, nephroblastoma, neuroblastoma, pancreatoblastoma, pleuropulmonary blastoma, retinoblastoma and glioblastoma-multiforme. Each possibility represents a separate embodiment.

In some embodiments, the NOTCH-associated disease is selected from: T cell acute lymphoblastic leukemia (T-ALL), Chronic lymphocytic leukemia (CLL), Melanoma, Cholangiocarcinoma (CCC), Colorectal cancer, Lung adenocarcinoma, Glioblastoma, Renal cell carcinoma, Ovarian cancer, Prostate cancer, Breast cancer, Pancreatic ductal adenocarcinoma (PDAC), Cervical cancer, Head and neck squamous cell carcinomas (HNSCC), Hepatocellular carcinoma (HCC), Medulloblastoma, B cell acute lymphoblastic leukemia (B-ALL), Acute myeloid leukemia (AML), Small cell lung carcinoma (SCLC), Lung squamous cell carcinoma (SqCC), Cutaneous squamous cell carcinoma (SqCC), Chronic myelomonocytic leukemia (CMML), chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder. Each possibility represents a separate embodiment.

In some embodiments, a cell proliferation disease comprises or is inflammation.

In some embodiments, a cell proliferation disease comprises or is any of the following: Cutaneous T-cell lymphoma (CTCL) including Mycosis fungoides and Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, B cell malignancy, T cell lymphoma, Pancreatic cancer, Nasopharyngeal carcinoma, Squamous cell carcinoma, Prostatic adenocarcinoma, Non-small-cell lung carcinoma (NSCLC), Infantile myofibromatosis (IM), lateral meningocele syndrome, and desmoid tumor. Each possibility represents a separate embodiment.

In some embodiments, a cell proliferative disease comprises or is any one of the following: Mycosis fungoides, Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, Nasopharyngeal carcinoma, Infantile myofibromatosis (IM), lateral meningocele syndrome, and desmoid tumor. Each possibility represents a separate embodiment.

In some embodiments, a composition for use in the treatment of: Cutaneous T-cell lymphoma (CTCL) including Mycosis fungoides and Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, B cell malignancy, T cell lymphoma, Pancreatic cancer, Nasopharyngeal carcinoma, Squamous cell carcinoma, Prostatic adenocarcinoma, Non-small-cell lung carcinoma (NSCLC), Infantile myofibromatosis (IM), lateral meningocele syndrome, and desmoid tumor comprises a w/w ratio of (i) CF1 and (ii) at least one of CBD, CBDV, or any combination thereof, selected from 1,000:1 to 1:1,000, 1,000:1 to 1:1, 750:1 to 1:1, 500:1 to 1:1, 300:1 to 1:1, 100:1 to 1:1, 1:1 to 1:100, 1:1 to 1:300, 1:1 to 1:500, 1:1 to 1:750, and 1:1 to 1:1,000. Each possibility represents a separate embodiment.

In some embodiments, a composition for use in the treatment of: Mycosis fungoides, Sézary syndrome, Intestinal and diffuse-type gastric cancer, Pilocytic astrocytoma (PA), Choroid plexus tumor, Laryngeal squamous cell carcinoma (LSCC), Gallbladder carcinoma, Kaposi's sarcoma, Nasopharyngeal carcinoma, Infantile myofibromatosis (IM), lateral meningocele syndrome, and desmoid tumor comprises a w/w ratio of (i) CF1 and (ii) at least one of CBD, CBDV, or any combination thereof, selected from 1,000:1 to 1:1,000, 1,000:1 to 1:1, 750:1 to 1:1, 500:1 to 1:1, 300:1 to 1:1, 100:1 to 1:1, 1:1 to 1:100, 1:1 to 1:300, 1:1 to 1:500, 1:1 to 1:750, and 1:1 to 1:1,000. Each possibility represents a separate embodiment.

In some embodiments, the NOTCH-related disease comprises or is any of the following: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder. Each possibility represents a separate embodiment.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a (i) CF1, CBDV, or both and (ii) CBD weight/weight (w/w) ratio of 1,000:1 to 1:1,000, 1,000:1 to 1:1, 500:1, to 5:1, 1:1 to 1:1,000, 1:5 to 1:500, 1:7 to 1:225, or 1:30 to 1:900. Each possibility represents a separate embodiment. In some embodiments, the composition comprises a (i) CF1, CBD, or both, and (ii) CBDV w/w ratio of 1,000:1 to 1:1,000, 1,000:1 to 1:1, 750:1 to 1:750, 500:1 to 1:500, 300:1 to 1:300, or 1:1 to 1:1,000. Each possibility represents a separate embodiment. In some embodiments, the composition comprises a (i) CBD, CBDV, or both, and (ii) CF1 w/w ratio of 1,000:1 to 1:1,000, 1,000:1 to 1:1, 750:1 to 100:1, 500:1 to 1:1, 300:1 to 1:1, 1:1 to 1:300, 1:1 to 1:500, 1:1 to 1:750, or 1:1 to 1:1,000. 1,000:1 to 1:1,000. Each possibility represents a separate embodiment.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a w/w ratio of (i) CF1 and (ii) at least one of CBD, CBDV, or any combination thereof, selected from 1,000:1 to 1:1,000, 1:1 to 1:1,000, 1:1 to 800:1, 1:1 to 1:500, 1:1 to 1:300, 1:1 to 1:200, 1:1 to 1:100, 1:1 to 1:50, 1:1 to 1:20, 1:1 to 1:15, 15:1 to 1:1, 20:1 to 1:1, 50:1 to 1:1, 100:1 to 1:1, 200:1 to 1:1, 300:1 to 1:1, 500:1 to 1:1, 800:1 to 1:1, and 1,000:1 to 1:1, wherein each possibility represents a separate embodiment of the invention.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a w/w ratio of (i) CBD and (ii) at least one of CF1, CBDV, or any combination thereof, selected from 1,000:1 to 1:1,000, 1,000:1 to 100:1, 250:1 to 400:1, 1:1 to 800:1, 1:1 to 350:1, 1:1 to 300:1, 1:1 to 70:1, 1:1 to 50:1, 1:1 to 20:1, 1:20 to 1:1, 1:50 to 1:1, 1:70 to 1:1, 1:300 to 1:1, 1:350 to 1:1, 1:800 to 1:1, 1:400 to 1:250, and 1:100 to 1:1,000, wherein each possibility represents a separate embodiment of the invention.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a w/w ratio of (i) CBDV and (ii) at least one of CF1, CBD, or any combination thereof, selected from 1,000:1 to 1:1,000, 1:1 to 1:1,000, 50:1 to 1:500, 1:1 to 1:100, 1:1 to 1:50, 1:1 to 1:300, 1:1 to 1:250, 1:1 to 1:10, 1:1 to 1:90, 1:1 to 1:20, 1:1 to 1:1.5, 1.5:1 to 1:1, 20:1 to 1:1, 90:1 to 1:1, 10:1 to 1:1, 250:1 to 1:1, 300:1 to 1:1, 50:1 to 1:1, 100:1 to 1:1, 500:1 to 1:50, and 1,000:1 to 1:1, wherein each possibility represents a separate embodiment of the invention.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a w/w ratio of CF1 to CBD of at least 1:1,000, 1:800, 1:600, 1:400, 1:350, 1:200, 1:100, 1:10, 1:1, or any value and range therebetween. Each possibility represents a separate embodiment of the invention.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a w/w ratio of CF1 to CBDV of at least 1:1,000, 1:800, 1:600, 1:400, 1:350, 1:200, 1:100, 1:10, 1:1, or any value and range therebetween. Each possibility represents a separate embodiment of the invention.

In some embodiments, a composition for use in the treatment of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder comprises a w/w ratio of CBDV to CBD of at least 1:10, 1:20, 1:50, 1:60, 1:150, 1:200, 1:300, 1:500, or any value and range therebetween. Each possibility represents a separate embodiment of the invention. In some embodiments, a composition as described comprises or has w/w ratio of CBDV to CBD of at least 100:1, 50:1, 25:1, 10:1, 5:1, 2:1, or any value and range therebetween. Each possibility represents a separate embodiment of the invention.

One skilled in the art will appreciate that NOTCH receptor functions as ligand-activated transcription factor to directly transduce extracellular signals into changes in gene expression in the nucleus. Each receptor has an N-terminal extracellular (NEC) fragment responsible for interaction with ligands for example from the Delta and Serrate family (e.g. Delta-like 1, 3, and 4; and Jagged 1 and 2). Three Lin12/NOTCH repeats (LNR) in the NEC fragment fold over a heterodimerization domain (HD), stabilizing and shielding the HD domain in a molecular lock that prevents NOTCH activation in the absence of a ligand. Each receptor also comprises a C-terminal transmembrane-intracellular fragment (NTM) having a single-pass transmembrane domain and a cytoplasmic region which functions as a ligand-activated transcription factor. The intracellular portion of the NOTCH receptor (termed N1ICD) is translocated into the nucleus to mediate target gene activation. The N1ICD consists of ankyrin repeats, a RAM (RBP-Jk associated molecule) domain, a transactivation domain (TAD), a nuclear localization signal (NLS), and a PEST [proline (P), glutamic acid (E), serine (S), and threonine (T) rich] domain, responsible for terminating NOTCH1 signaling by targeted proteasome degradation of the activated receptor in the nucleus. Each receptor is generated by proteolytic cleavage of a pro-NOTCH1 precursor polypeptide by a furin-like protease in the trans-Golgi network. Triggering of the NOTCH receptor by ligand-binding promotes two proteolytic cleavage events at the NOTCH receptor. The first cleavage is catalyzed by the ADAM-family of metalloproteases, whereas the second cleavage is mediated by γ-secretase. The second cleavage releases the N1ICD, which is then translocated to the nucleus and acts as a transcriptional coactivator. The N1ICD cannot bind directly to DNA but heterodimerizes with the DNA binding recombination signal sequence-binding protein Jkappa (RBP-J), (also called CSL, CBF1, [Su(H)] and LAG-1) and activates transcription of genes containing RBP-J binding sites such as HES1 and c-Myc. In the absence of a ligand and without nuclear N1ICD, RBP-J represses NOTCH target genes. Evidence for the involvement of NOTCH signaling in cancer can be seen in FIGS. 6A-6D.

According to some embodiments, the subject to be treated by the cannabinoids and compositions of the invention comprises at least one cell comprising an abnormal expression level of the NOTCH protein compared to control cells (e.g. cells having a normal NOTCH expression level). In some embodiments, the abnormal expression level relates to increased NOTCH protein expression level. In some embodiments, the abnormal level of a NOTCH protein relates to decreased expression level of a NOTCH protein. In some embodiments, the NOTCH-related disease relates to a mutation in the NOTCH gene. In some embodiments, the NOTCH-related disease relates to a mutation in a NOTCH-associated gene. In some embodiments, the subject is characterized by having at least one cell comprising an abnormal expression of a NOTCH protein.

Methods for determining NOTCH expression are common and would be apparent to one of ordinary skill in the art. Non-limiting examples of methods for determining expression include, but are not limited to, RT-PCR, real time RT-PCR, next generation sequencing, western blot, dot blot, enzyme linked immunosorbent assay (ELISA), and others.

According to some embodiments, a subject afflicted with a NOTCH-related disease comprises at least one mutation in a NOTCH gene. In some embodiments, a mutation is a missense mutation. In some embodiments, a mutation is a nonsense mutation. In some embodiments, a mutation is a frameshift mutation. In some embodiments, a mutation results in a shorter protein encoded from the mRNA harboring the mutation. In some embodiments, a mutation renders a nonfunctional protein encoded from an mRNA harboring the mutation.

According to some embodiments, the mutation is at a NOTCH extracellular (NEC) fragment. According to some embodiments, the mutation is at a NOTCH transmembrane-intracellular fragment. According to some embodiments, the mutation is at a domain selected from Lin12/NOTCH repeat (LNR), heterodimerization domain (HD), intracellular portion of the NOTCH receptor (N1ICD), ankyrin repeat, RAM domain, TAD domain, NLS, and a PEST. Each possibility represents a separate embodiment.

As used herein, the term "NOTCH-associated gene", in some embodiments, refers to genes which are activated by NOTCH. Non-limiting example of genes which are activated by NOTCH include, LFNG, SNW1, NFKB1, HIF1A, RBPJ, HEYL, TCFL5, ADAM19, BCL11B, HEY1, HES1, PIN1, NFKB2, ERBB2, FABP7, PPARG, PAX7, C-MYC, HES1, HOXA5, BCL2, IL7R, TCF12, CD44, and IL2RA. Each possibility represents a separate embodiment. In some embodiments, the term "NOTCH-associated gene", refers to genes which are inactivated by NOTCH. A non-limiting example of a gene which is inactivated by NOTCH includes TCF3. In some embodiments, the term "NOTCH-associated gene" refers to genes which activate NOTCH. Non-limiting examples of genes which activate NOTCH include MAML1, MAML2, PSEN1, KAT2B, SNW1, TNF, DLL4, MFNG, GXYLT1, GXYLT2, JAG1, DLL1, DLL3, CTNNB1, DTX1, CNTN6, LFNG, PIN1, RFNG, POGLUT1, LCK, KPNA3, KPNA4, TCF3, DAB1, GSK3B, SMAD3, POFUT1, EIF3F, CCND1, SDC3, SIAH1, KPNA6, DNER, XXYLT1, CSK, FURIN, JAG2, MDM2, and ADAM17. Each possibility represents a separate embodiment. In some embodiments, the term "NOTCH-associated gene" refers to genes which inactivate NOTCH. Non-limiting examples of genes which inactivate NOTCH include CCNC, FBXW7, SIRT1, GSK3A, CDK8, DLK2, DYRK1A, RUNX2, FOXO3, NUMB, HIF1AN, KAT5, RUNX3, MAPK8IP1, ITCH, NLK, DLK1, HEY2, and YY1. Each possibility represents a separate embodiment.

In some embodiments, the composition of the invention reduces the viability of a cell. In some embodiments, the cell comprises a mutation in a NOTCH encoding gene. In some embodiments, the cell is a cell of a subject afflicted with a NOTCH-related disease. In some embodiments, the cell viability is reduced by at least 5%, 10%, 15%, 20%, 30%, 40%, 50%, 60%, 70%, 80%, or 90% and up to 100% compared to an untreated cell, or any value and range therebetween. Each possibility represents a separate embodiment of the invention. In some embodiments, cell viability reduction is at most 90%, 80%, 70%, 60%, 50%, 40%, 30%, 20% or 10% compared to untreated cells. Each possibility represents a separate embodiment of the invention.

In some embodiments, the composition induces apoptosis of the cell comprising a mutation in a NOTCH encoding gene. In some embodiments, the composition of the invention or an extract as disclosed herein induce apoptosis in at least 5%, 10%, 15%, 20%, 30%, 35%, 40%, 45%, 50%, 55%, 60%, 65%, 70%, 75%, 80%, 85%, 90%, 95%, or 99% and up to 100% of the cells, e.g., cells comprising a mutation in a NOTCH encoding gene, compared to untreated cells, or any value and range therebetween. Each possibility represents a separate embodiment of the invention.

In some embodiments, the composition induces apoptosis of the cell comprising over activation of NOTCH signaling. In some embodiments, the composition of the invention or an extract as disclosed herein induce apoptosis in at least 5%, 10%, 15%, 20%, 30%, 35%, 40%, 45%, 50%, 55%, 60%, 65%, 70%, 75%, 80%, 85%, 90%, 95%, or 99% and up to 100% of the cells, e.g., cells comprising over activation of NOTCH signaling, compared to untreated cells, or any value and range therebetween. Each possibility represents a separate embodiment of the invention.

In some embodiments, the cannabinoids and compositions of the invention reduce or increase the expression level of NOTCH and/or a NOTCH-associated gene, or the protein products thereof, in a cell comprising a mutation in a NOTCH encoding gene, e.g., a mutation indicative of NOTCH-related disease in a subject comprising the mutation. In some embodiments, protein expression level is reduced or increased by at least 5%, 10%, 15%, 20%, 30%, 40%, 50%, 60%, 70%, 80%, 90%, or 95% and up to 100% compared to a control, or any value and range therebetween. Each possibility represents a separate embodiment of the invention. In some embodiments, protein expression level of NOTCH and/or NOTCH-associated gene is at most 99%, 90%, 80%, 70%, 60%, 50%, 40%, 30%, 20% or 10% compared to a control. Each possibility represents a separate embodiment of the invention.

In some embodiments, a control is an untreated cell. In some embodiments, a control is the expression of a gene or a protein product thereof, or both, in an untreated cell.

The term "expression" as used herein refers to the biosynthesis of a gene product, including the transcription and/or translation of said gene product. Thus, expression of a nucleic acid molecule may refer to transcription of the nucleic acid fragment (e.g., transcription resulting in mRNA or other functional RNA) and/or translation of RNA into a precursor or mature protein (polypeptide).

In some embodiments, the cannabinoids and compositions of the invention inhibit cell proliferation of a cell comprising a mutation in a NOTCH encoding gene.

In some embodiments, the proliferation rate of a cell contacted with the cannabinoids and compositions of the invention is reduced or inhibited by at least 5%, 10%, 15%, 20%, 30%, 40%, 50%, 60%, 70%, 80%, or 90% and up to 100% compared to a control cell, or any value and range therebetween. Each possibility represents a separate embodiment of the invention.

In some embodiments, compositions for use in the methods of this invention comprise solutions or emulsions, which in some embodiments are aqueous solutions or emulsions comprising a safe and effective amount of the cannabinoids of the present invention and optionally, other compounds as described herein, including excipients intended for topical intranasal administration.

In another embodiment, the composition is administered by intravenous, intra-arterial, or intramuscular injection of a liquid preparation. In some embodiments, liquid formulations include solutions, suspensions, dispersions, emulsions, oils and the like. Each possibility represents a separate embodiment. In one embodiment, the composition is administered intravenously, and is thus formulated in a form suitable for intravenous administration. In another embodiment, the composition is administered intra-arterially, and is thus formulated in a form suitable for intra-arterial administration. In another embodiment, the composition is administered intramuscularly, and is thus formulated in a form suitable for intramuscular administration.

Further, in another embodiment, the composition is administered topically to body surfaces, and is thus formulated in a form suitable for topical administration. Suitable topical formulations include gels, ointments, creams, lotions, pastes, drops and the like. Each possibility represents a separate embodiment. For topical administration, the active ingredient(s) disclosed herein, e.g., one or more cannabinoids, are prepared and applied as solutions, suspensions, or emulsions in a physiologically acceptable diluent with or without a pharmaceutical carrier.

In one embodiment, the preparations described herein are formulated for parenteral administration (i.e. subcutaneous administration, intravenous administration, or intramuscular administration), e.g., by bolus injection or a continuous infusion. In some embodiments, formulations for injection are presented in unit dosage forms, e.g., in ampoules or in multidose containers with optionally, an added preservative. In some embodiments, the composition is a suspension, a solution or an emulsion in an oily or aqueous vehicle, and contains a suspending, a stabilizing and/or a dispersing agent.

In some embodiments, a composition for parenteral administration includes aqueous solution of the active preparation in water-soluble form. Additionally, suspensions of the active ingredients, in some embodiments, are prepared as appropriate oily or water-based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredient(s) to allow for the preparation of highly concentrated solutions.

In another embodiment, the composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989)). In another embodiment, further polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (*Science* 249:1527-1533 (1990)).

Compositions are formulated, in some embodiments, for atomization and inhalation administration. In another embodiment, compositions are contained in a container with attached atomizing means.

In one embodiment, the preparations of the present invention are formulated as rectal compositions such as suppositories or retention enemas, using, e.g., conventional suppository bases such as cocoa butter or other glycerides.

In one embodiment, the amount of a composition to be administered will be dependent on the subject being treated, the severity of the NOTCH-related disease, the manner of administration, etc. and can be determined according to the judgment of the prescribing physician.

In some embodiments, preparation of effective amount or dose can be estimated initially from in vitro assays. In one embodiment, a dose can be formulated in animal models, and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in humans. In one embodiment, the dosages vary depending upon the dosage form employed and the route of administration utilized. In one embodiment, the exact formulation, route of administration and dosage can be chosen by the individual physician in view of the patient's condition. (See e.g., Fingl, et al., (1975) "The Pharmacological Basis of Therapeutics", Ch. 1 p.1).

The dosage administered will be dependent on the age, health, and weight of the recipient, mode of concurrent treatment, if any, frequency of treatment, and the nature of the effect desired.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "about" when combined with a value refers to ±10% of the reference value.

It is noted that as used herein and in the appended claims, the singular forms "a", "an", and "the" include plural referents unless the context clearly dictates otherwise. Thus, for example, reference to "a cannabinoid" includes a plurality of such cannabinoids and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a composition having at least one of A, B, and C" would include, but not be limited to, compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), 3rd Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Phytocannabinoids Extraction

Air-dried medical *Cannabis* female flowers were ground to a fine powder using an electrical grinder. Several samples were heat-decarboxylated in an oven at 130° C. for 1 h. Approximately 5 g from each chemovar were accurately weighed and extracted with 50 mL HPLC-grade ethanol. Samples were sonicated in an ultrasonic bath for 30 min and then agitated in an orbital shaker at 25° C. for 15 min. Samples were then filtered under pressure through Whatman filter paper number 4 and the ethanol was evaporated under reduced pressure at 38° C. using a rotary evaporator.

The *Cannabis* extracts were analyzed as described in WO 2020/230145, the contents of which are incorporated by reference herein in their entirety.

The average contents of CF1, CBD and CBDV in the various extracts used are detailed in Table 1.

TABLE 1

| Extract | % CF1 | % CBD | % CBDV |
|---|---|---|---|
| CAN2 | 1.3 | 44.6 | 1.4 |
| CAN6 | 0.02 | 0.15 | 0.03 |
| CAN12 | 2.7 | 53.4 | 2.9 |
| CAN26 | 1.1 | 52.2 | 0.07 |

Statistical analysis included one-way ANOVA, Dunnett's multiple comparisons test. Data shown is presented as the average (±SEM) of three different experiments. Statistically significant differences are relative to control with a $P<0.05$.

Example 1

*Cannabis* Extract Affects Survival and Expression Profile of Colon Cancer Cells The effects of cannabinoids on the survival and NOTCH signaling of colon cancer cells (LS-1034) harboring the adenomatous polyposis coli (APC) mutation were examined.

Human colon carcinoma cell line (LS-1034) was incubated for 24 hours with three *Cannabis* extracts denoted CAN2, CAN6, and CAN12 (6 μg/mL) or with DMSO as control. Apoptosis was assessed by cleaved caspase 3 induction using western blot analysis. Cells were lysed and resolved on SDS-PAGE followed by western blotting with anti-cleaved caspase 3 and anti β-Tubulin antibodies. Quantification of cleaved caspase 3 levels following incubation with extracts relative to control and adjusted to β-Tubulin as loading control was performed.

Figure 1B:
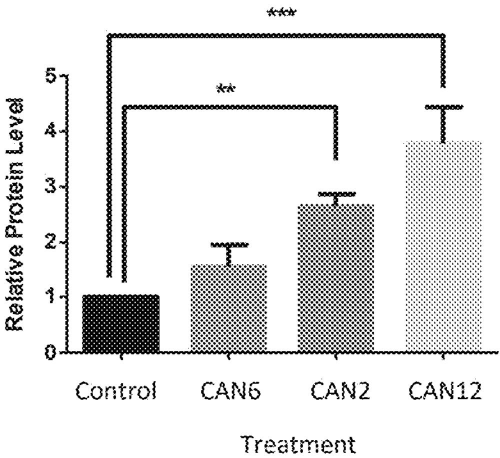

FIG. 1A shows the western blots of cells that were lysed and resolved on SDS-PAGE followed by western blotting with anti-cleaved caspase 3 and anti β-Actin antibodies. FIG. 1B shows the quantification of cleaved caspase 3 levels following incubation with the extracts, relative to control and adjusted to β-Tubulin as loading control. Data are presented as average±SEM of three different experiments. Asterisks indicate statistically significant differences compared to control (*$P<0.05$; one-way ANOVA, Dunnett's multiple comparisons test).

The results show that several *Cannabis* extracts increase the amount of cleaved caspase 3, thereby promoting apoptosis (FIGS. 1A-1B).

Figure 1C:
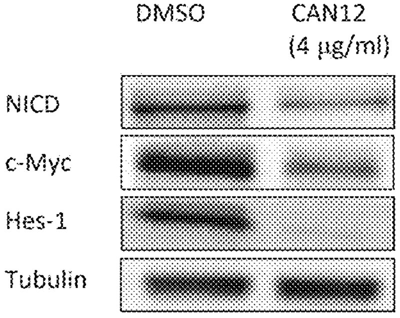

FIG. 1C shows the protein levels of NICD, c-Myc, HES1, and Tubulin in mice derived intestinal organoids. Untreated APC Min organoids and APC Min organoids treated with CAN12 were lysed and resolved on SDS-PAGE followed by western blotting with anti-NICD, anti-HES1, anti Myc, and anti β-Tubulin antibodies.

The results show that the expression levels of NICD, cMyc, and Hes1 in the presence of *Cannabis* extract 12 were substantially reduced (FIG. 1C).

Example 2

Cannabinoids Reduce the Survival of Cancer Cells Harboring a NOTCH 4 Mutation The effects of cannabinoids on the survival of tolerant glioblastoma (GBM) cancer cells harboring a NOTCH 4 mutation were examined.

Figure 2A:
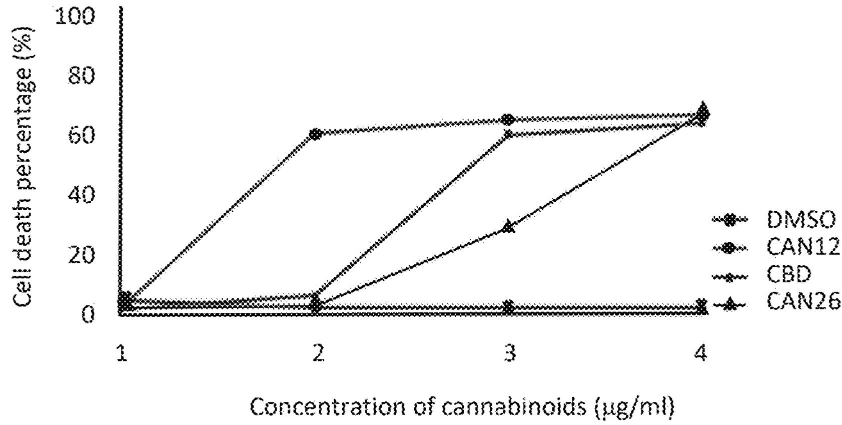
FIGS. 2A-2B show DBTRG-05MG cell death after treatment with *Cannabis* extracts (2A) and purified molecules from the CAN 12 extract (2B).

DBTRG-05MG cells were cultured in 96 well plate ($1\times10^5$ cells/well) until confluency and treated with DMSO as control, pure cannabidiol (CBD), and extracts CAN12 and CAN26 with increasing concentrations from 1 to 4 μg/ml (FIG. 2A).

Figure 2B:
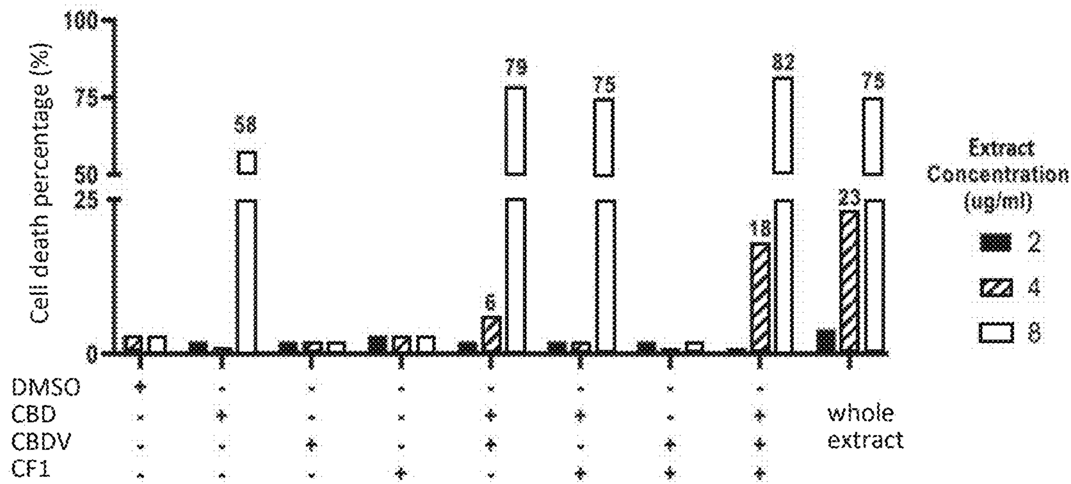

In another experiment, cells were cultured in 96 well plate ($1\times10^5$ cells/well) until confluency and treated for 24 hours with three molecules (CBD, CBDV and CF1) as compared to the whole extract. The treatments were performed using three extract concentrations: 2, 4 and 8 μg/ml (FIG. 2B). After 24 hours, cells were stained with Hoechst and Propidium Iodide (PI) and imaged by IXM micro system (Molecular Devices) in 10× magnification. Live and dead cells were analyzed by MetaXpress® software (Molecular Devices) and presented as percentages of cell death from total cells. The purified phytocannabinoids were diluted to contain the same content as in the extract, then were provided according to the extract concentrations.

The results show that *Cannabis* extract 12 (CAN12) and cannabidiol (CBD) alone increased the % of cell death among GBM cancer cells (FIGS. 2A-2B). Furthermore, either CBDV, CF1, or both, improved the activity of CBD alone (FIG. 2B). The combination of CBD, CBDV, and CF1 presented an activity which was comparable or even slightly superior to the whole extract (FIG. 2B).

Example 3

Cannabinoids Affect DOX-resistant Breast Cancer Cells

The effects of cannabinoids on the expression level of NICD in the presence of doxorubicin (DOX) alone were examined.

Figure 3A:
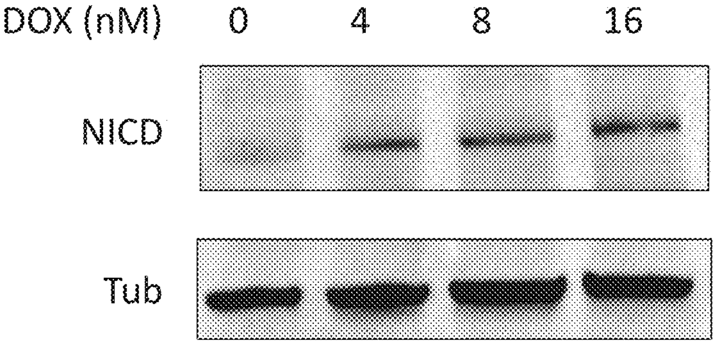
FIGS. 3A-3B show the effect of cannabinoids on doxorubicin (DOX)-resistant MCF-7 cell lines.
Figure 3B:
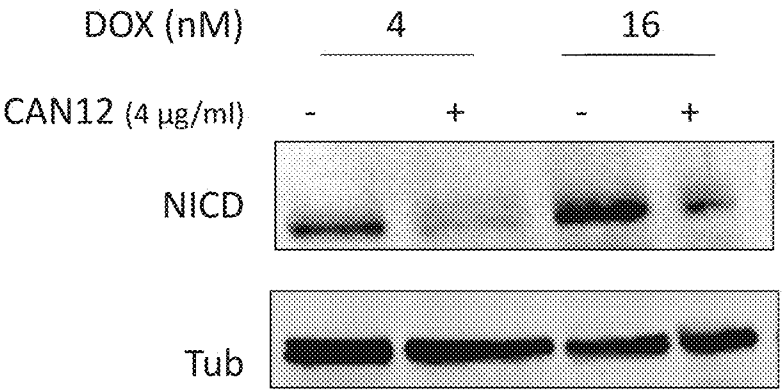

MCF-7/WT cells were cultured with 1 nM DOX or with DOX deprivation for 14 days. After the cells were tolerable, drug concentration was doubled until the cells acquired resistance. Followed by repeated treatments, cell lines were established with incremental strength of resistance to DOX ranging from 1 nM to 16 nM, and NICD expression level was analyzed by western blot analysis and normalized to β-tubulin level (FIG. 3A). MCF-7/WT, MCF-7/DOX-2, and MCF-7/DOX 4 cell lines were treated with extract CAN12 at 4 μg/ml or with vehicle treatment for 24 hours. NICD expression level was analyzed by western blot analysis and normalized to β-tubulin level (FIG. 3B).

Breast cancer cells with developing tolerance to increasing levels of doxorubicin showed increasing levels of the intracellular domain of the NOTCH protein (NICD; FIG. 3A). In sharp contrast, supplementing the breast cancer cells with a *Cannabis* extract (e.g., CAN12) significantly reduced the levels of NICD, both at the low and high concentrations of DOX, i.e., 4 nM and 16 nM, respectively (FIG. 3B).

Example 4

Modification of Cannabinoids Ratio Improves Apoptotic Activity

In order to determine whether specific ratios among cannabinoids, e.g., CBD, CBDV, and CF1, improve the apoptotic activity induced by the cannabinoids, the survival rates of cancer cells which were exposed to compositions containing different cannabinoids at different ratios were assessed.

Dose-dependent AlamarBlue® (resazurin) viability assays were performed on Molt-4 cells treated with different concentrations of three phytocannabinoids (CBD, CBDV and CF1) at different ratios, as shown in Table 2.

TABLE 2

| | A (ng/μl) | B (ng/μl) | C (ng/μl) | D (ng/μl) | E (ng/μl) | F (ng/μl) | G (ng/μl) |
|---|---|---|---|---|---|---|---|
| CBD | 0.5 | 0.44 | 0.32 | 0.08 | 0.44 | 0.32 | 0.08 |
| CBDV | 0.06 | 0.12 | 0.24 | 0.48 | 0.06 | 0.06 | 0.06 |
| CF1 | 0.06 | 0.06 | 0.06 | 0.06 | 0.12 | 0.24 | 0.48 |

Figure 4:
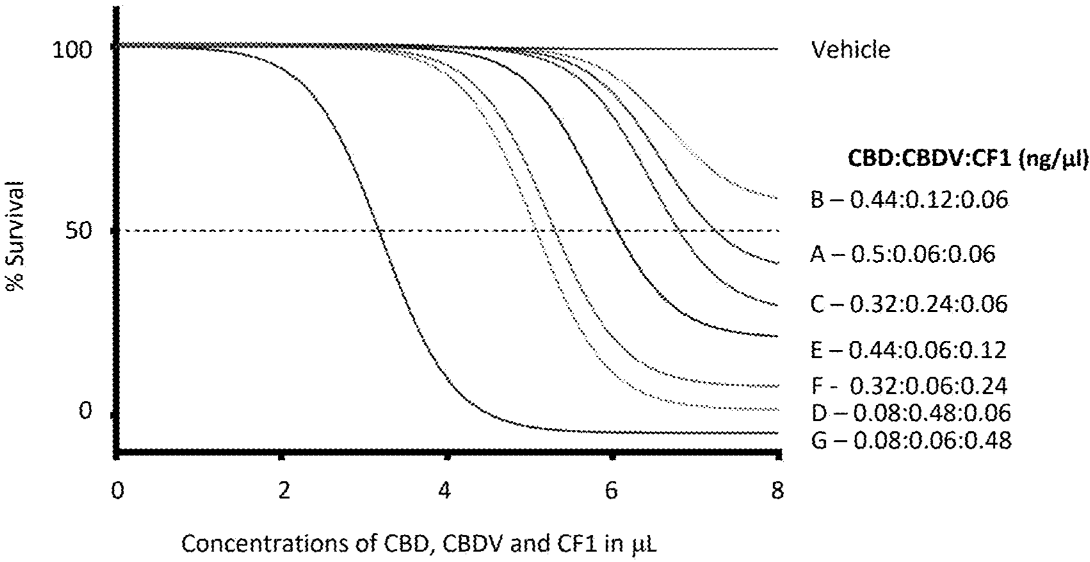
FIG. 4 shows dose-dependent AlamarBlue© viability assays performed on Molt-4 cells treated with different concentrations of three phytocannabinoids (CBD, CBDV and CF1) at different ratios.

Most compositions were shown to substantially reduce the survival rate of cancer cells (FIG. 4). For example, combination G was found to be highly effective in inducing apoptosis.

In order to determine the effect of cannabinoids on the reduction of the survival rate of cancer cells, dose-dependent AlamarBlue® (resazurin) viability assays were then performed on Molt-4 cells treated with single cannabinoids or a combination of two cannabinoids at the same concentration as that of the three phytocannabinoids present in the whole extract, as shown in Table 3. Particularly, CF1 alone, or in combination with one additional cannabinoid was examined to determine its capability to induce apoptosis of cancer cells.

TABLE 3

| | 1a (ng/μl) | 2a (ng/μl) | 3a (ng/μl) | 4a (ng/μl) | 5a (ng/μl) | 6a (ng/μl) |
|---|---|---|---|---|---|---|
| CBD | 0 | 0 | 0.14 | 0 | 0 | 0 |
| CBDV | 0 | 0.14 | 0 | 0.3 | 0.48 | 0.62 |
| CF1 | 0.62 | 0.48 | 0.48 | 0.32 | 0.14 | 0 |

Figure 5:
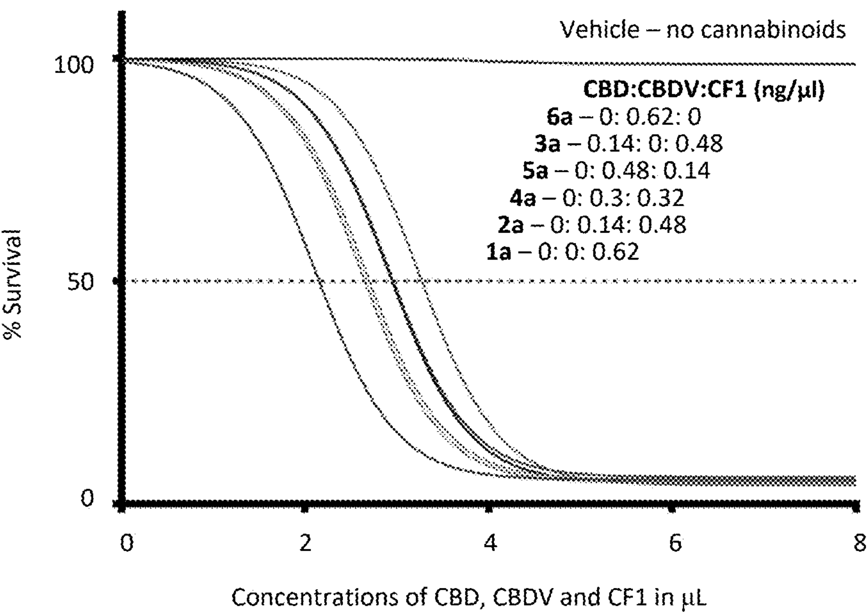
FIG. 5 shows dose-dependent AlamarBlue® (resazurin) viability assays performed on Molt-4 cells treated with different compositions of phytocannabinoids (CBD, CBDV and CF1) at different ratios or with a single phytocannabinoid at the same concentration of the three phytocannabinoids as present in the whole extract.
Figure 6A:
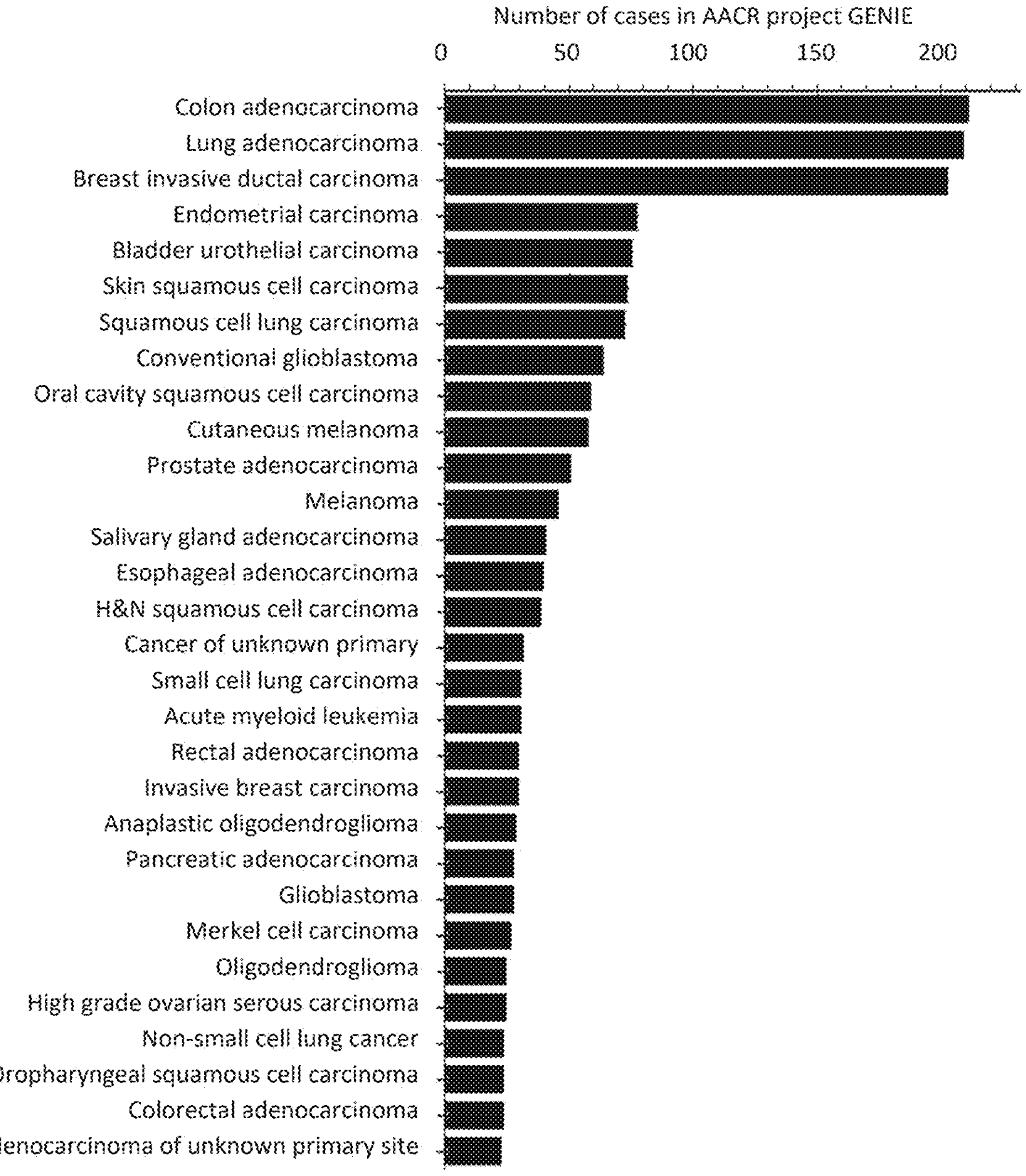
FIGS. 6A-6D show the involvement of NOTCH signaling in cancer. Specifically, the number of cases in American Association for Cancer Research (AACR) project GENIE is shown for NOTCH 1 (6A), NOTCH 2 (6B), NOTCH 3 (6C), and NOTCH 4 (6D).
Figure 6B:
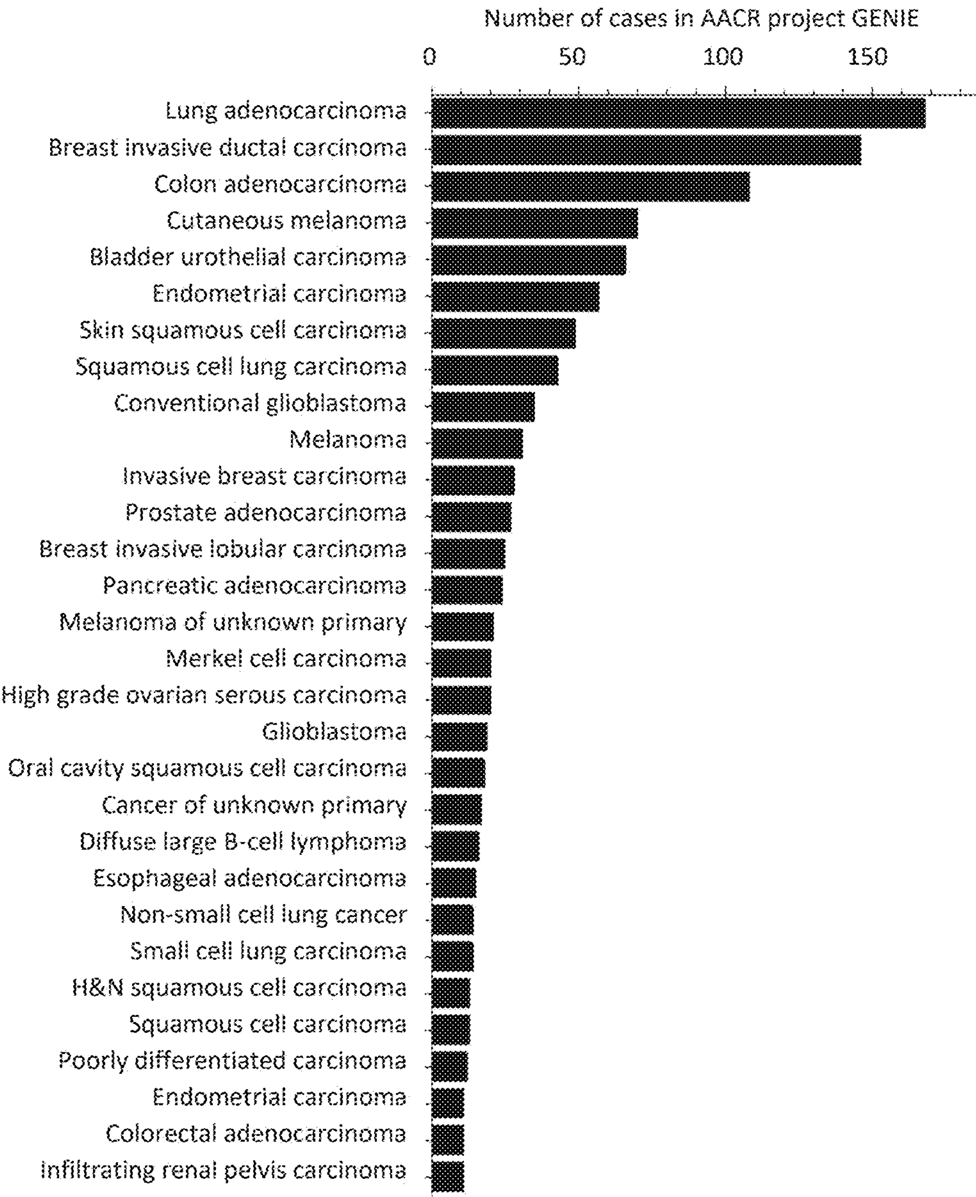
Figure 6C:
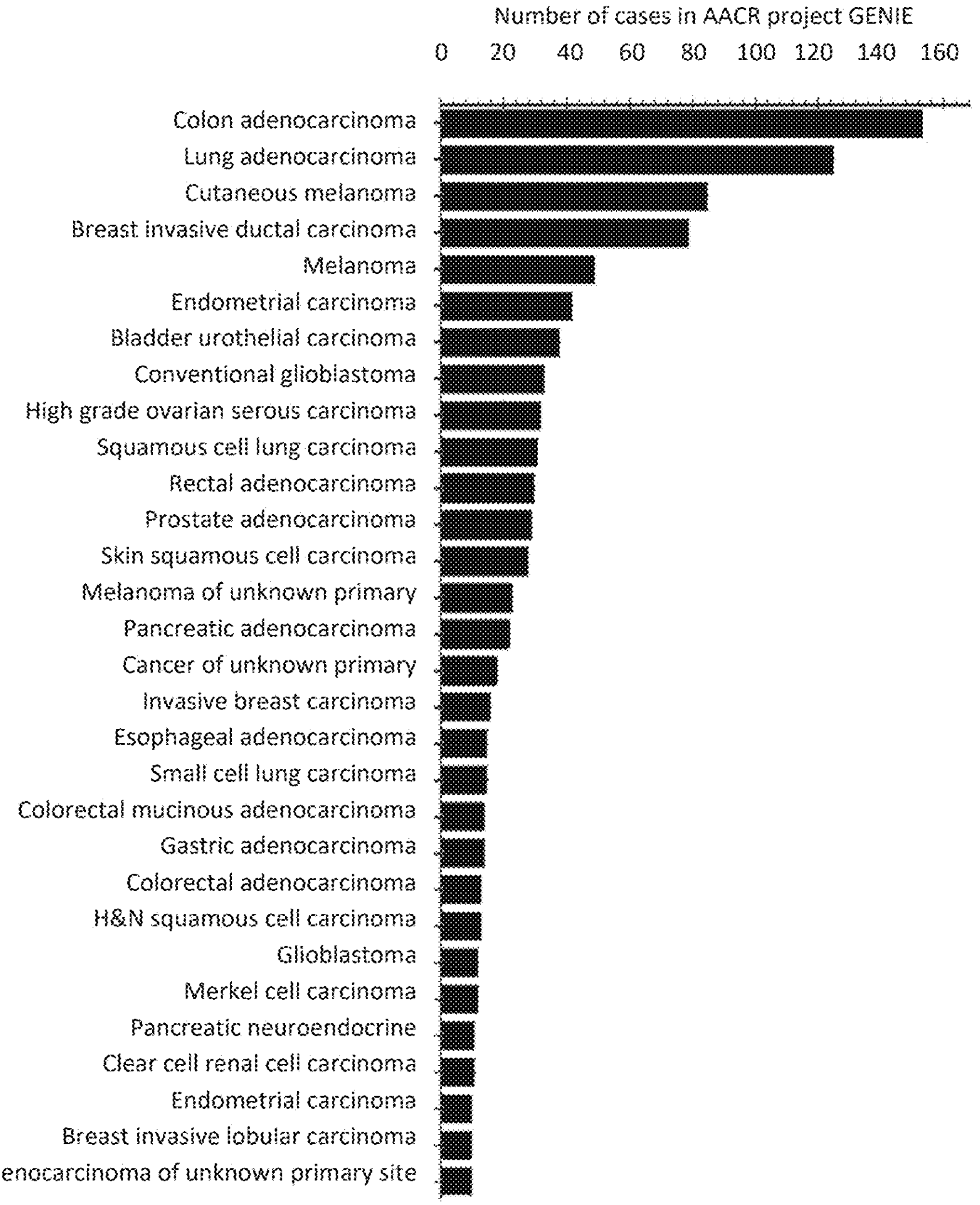
Figure 6D:
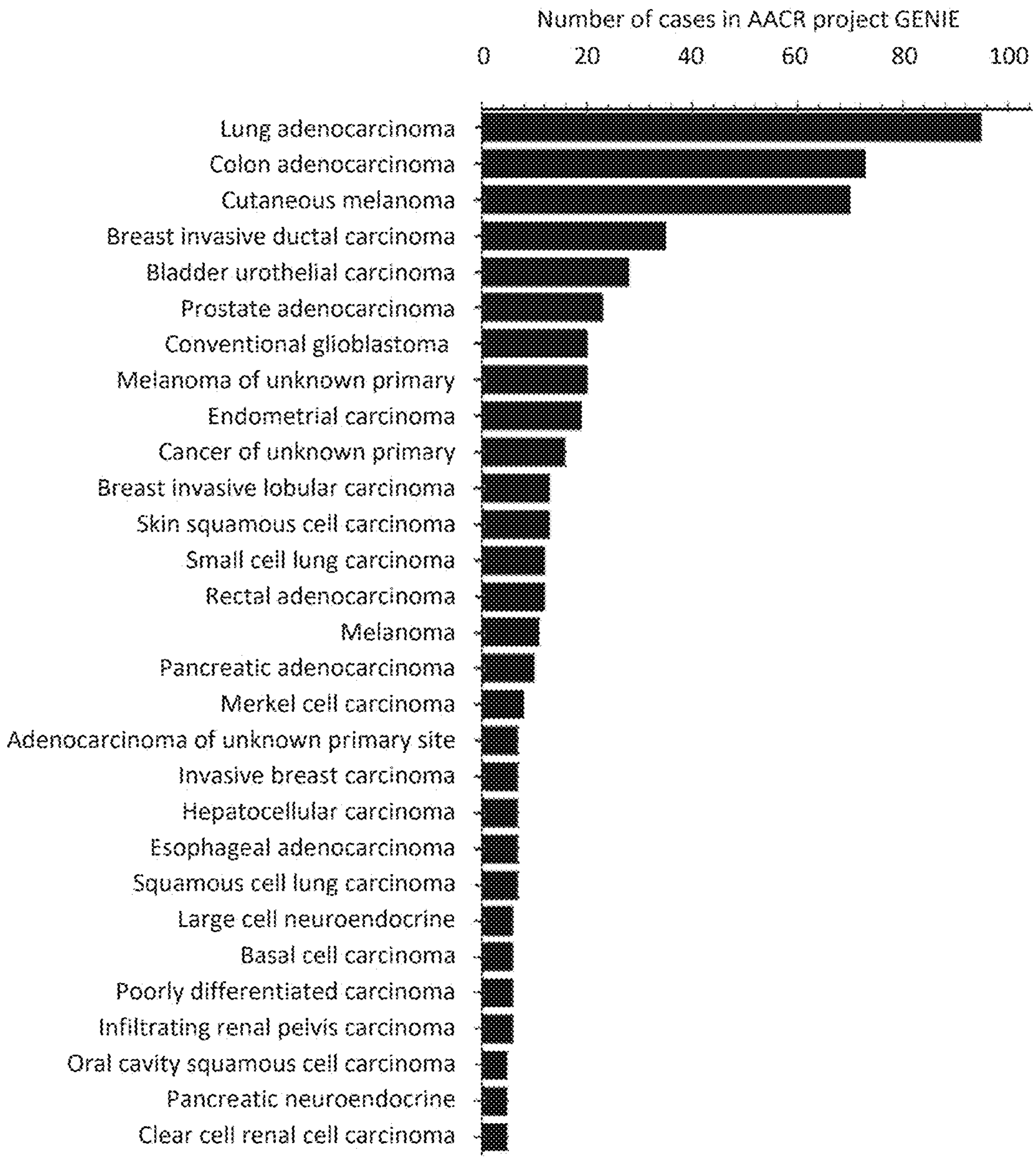

CF1 was found to be the most potent cannabinoid of the three and showed efficacy in inducing cancer cells death even when it was introduced alone as a single cannabinoid (FIG. 5, 1*a*).

Example 5

Cannabinoids Reduce the Survival of B-cell Lymphomas

The effects of cannabinoids on the survival of B-cell lymphomas cancer cells (mantle cell lymphoma (MCL) and Chronic lymphocytic leukemia (CLL)) were examined. All experiments were performed on $1\times10^6$ cells per treatment in a 12 well plate.

Figure 7A:
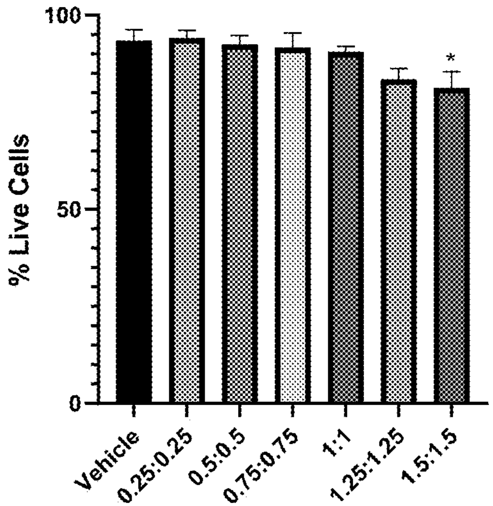
FIGS. 7A-7D show AlamarBlue® (resazurin) viability assays and typical western blots of JEKO-1 and REC1 cell lines following 24 h treatment with either vehicle or CBD:CF1 at a 1:1 ratio.
Figure 7B:
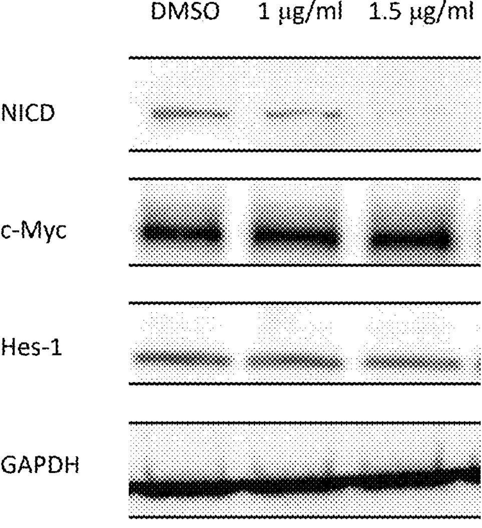
Figure 7C:
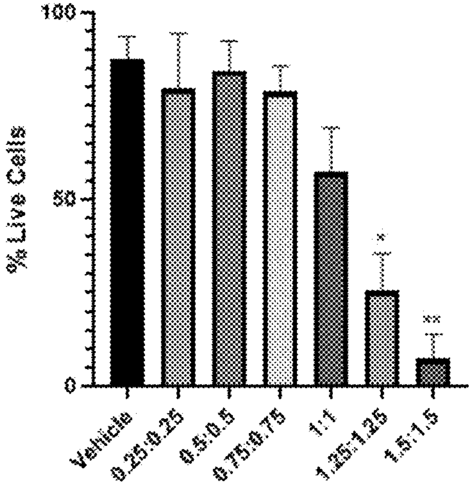

Analysis of apoptosis via an Annexin V assay on JEKO-1 and REC1 cell lines following 24 h treatment with either vehicle or CBD:CF1 at a 1:1 ratio (0.25 to 1.5 μg/mL each) was performed (FIGS. 7A and 7C, respectively). Data are presented as mean±SEM (n=3) and statistically analyzed by two-way ANOVA (*$p<0.05$, **$p<0.01$).

Figure 7D:
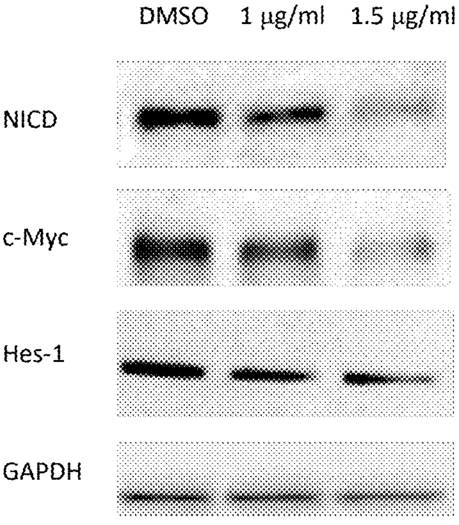

Representative blots of key proteins in NOTCH 1 signaling of JEKO1 and REC1 cell lines following 5 h treatment with vehicle or CBD:CF1 at a 1:1 ratio (0.25 to 1.5 μg/mL each) with GAPDH as the loading control are shown in FIGS. 7B and 7D, respectively.

The results show that CBD and CF1 at a 1:1 ratio reduced MCL cells survival in a dose dependent manner only in the REC-1 cell harboring a NOTCH mutation and not in the JEKO1 cell with a wildtype NOTCH. In addition, CBD and CF1 at a 1:1 ratio reduced NOTCH activity as seen in reduction of NICD and the downstream signaling of NOTCH cMYC and Hes1, only in the REC1 cells (FIG. 7D).

Figure 8A:
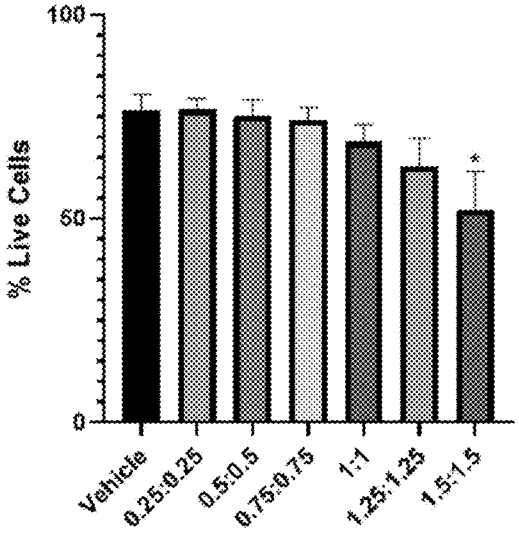
FIGS. 8A-8B show analysis of apoptosis via an Annexin V assay on I83-LCL and CII CLL cell lines following 24 h treatment with either vehicle or CBD:CF1 at a 1:1 ratio.
Figure 8B:
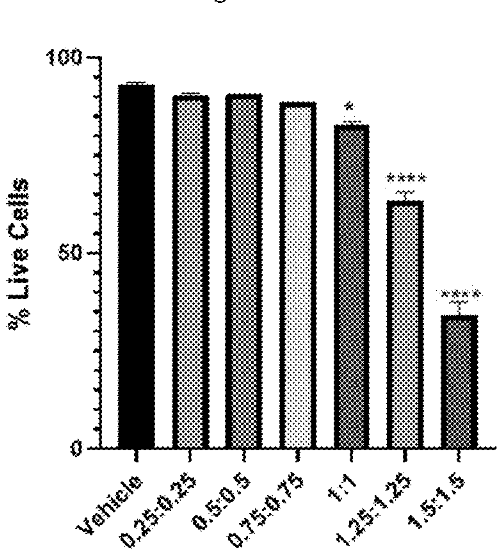

Analysis of apoptosis via an Annexin V assay on I83-LCL and CII CLL cell lines following 24 h treatment with either vehicle or CBD:CF1 at a 1:1 ratio (0.25 to 1.5 μg/mL each) was performed (FIGS. 8A and 8B, respectively). Data are presented as mean±SEM (n=3) and statistically analyzed by two-way ANOVA (*p<0.05, ****p<0.0001).

The results show that CBD and CF1 at a 1:1 ratio reduced the survival of CLL cell line CII in a dose dependent manner.

Example 6

Cannabinoids Reduce the Survival of Melanoma Cells Harboring a NOTCH 2 Mutation The effects of cannabinoids on the survival of Melanoma (A375) cells harboring a NOTCH 2 gain of function mutation were examined.

Analysis of apoptosis via an Annexin V assay on melanoma A375 cell line following 24 h treatment with either vehicle or *Cannabis* extract CAN12 at concentrations of 0.6125 to 10 μg/mL (N=1) was performed.

Figure 9:
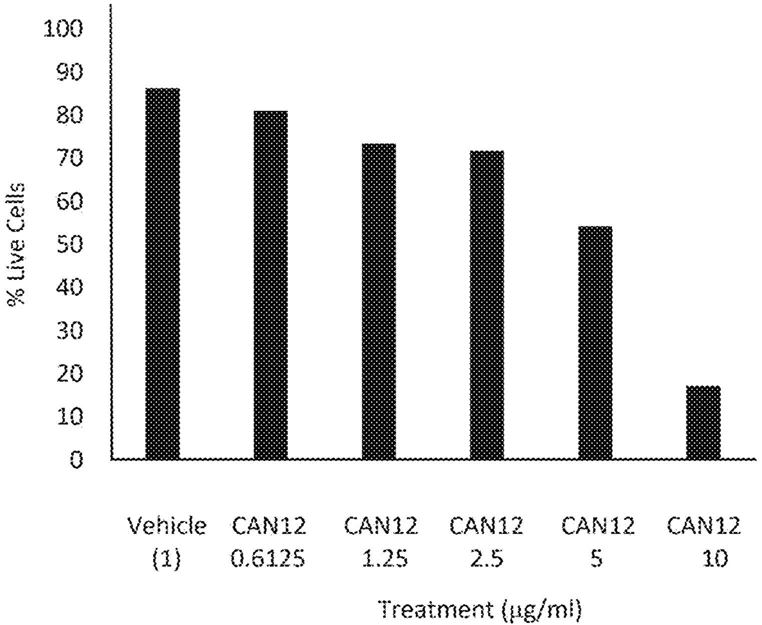
FIG. 9 shows analysis of apoptosis via an Annexin V assay on melanoma A375 cell line following 24 h treatment with either vehicle or CAN12 extract.

FIG. 9 shows the % of live cells as determined by FACS, indicating cell death induced by the treatment.

Example 7

Cannabinoids Effect on the Survival of Cutaneous T-cell Lymphoma

Figure 10A:
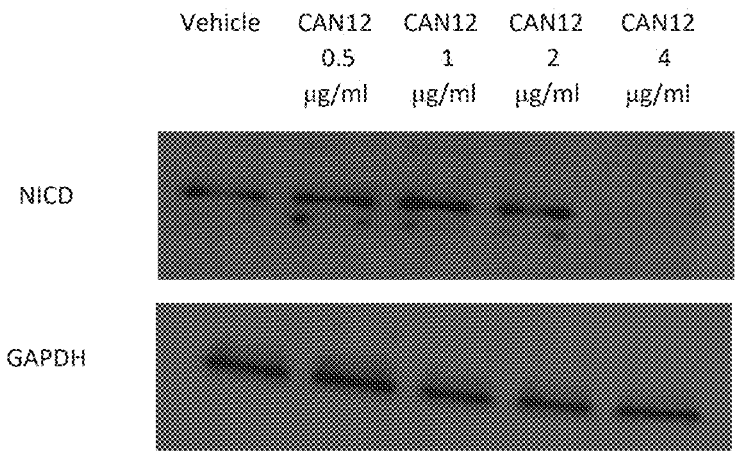
FIGS. 10A-10B show a representative blot of NICD and analysis of apoptosis via an Annexin V assay in Myla cell line following treatment with CAN12 extract and CBD:CF1 at a 1:1 ratio.
Figure 10B:
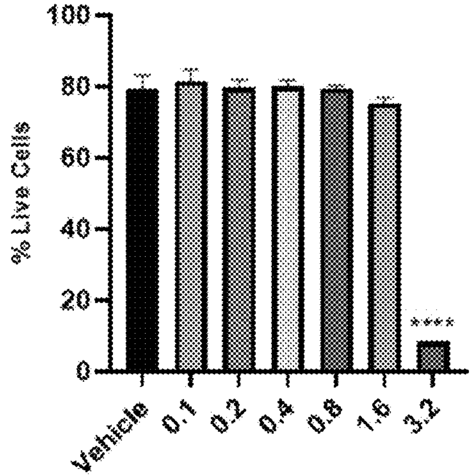

The effects of cannabinoids on the survival of and NOTCH signaling in cutaneous T-cell lymphoma, specifically Mycosis fungoides (My-La CD4+) over activation of NOTCH signaling were examined Cells ($1\times10^6$ cell per treatment in a 12 well plate) were exposed to *Cannabis* extract CAN12 for 24 h at concentrations of 0.5-4 μg/mL or to CF1:CBD at a 1:1 ratio and concentrations of 0.05 to 1.6 μg/mL each. Exposure of the cells to a vehicle was used as control. Apoptosis was examined by evaluating Annexin V assay. FIG. 10A shows representative blot of NICD in Myla cell line following 24 h treatment with vehicle or CAN12 at concentrations of 0.5 to 4 μg/mL with GAPDH as the loading control. FIG. 10B shows the % of live cells. Data are presented as mean±SEM and statistically analyzed by two-way ANOVA (*p<0.05, ****p<0.0001).

The results show that cell death is induced at concentrations of 3-4 μg/mL of either CAN12 extract or CF1:CBD at a 1:1 ratio.

Example 8

Cannabinoids Effect on the Survival of Cutaneous T-cell Lymphoma

The effects of cannabinoids on the survival of and NOTCH signaling in cutaneous T-cell lymphoma, specifically Sézary syndrome (HuT 78), over activation of NOTCH signaling are examined.

Cells are exposed to *cannabis* extracts, CBD or CF1 single cannabinoids or combinations thereof at concentrations of 0.5 μg/ml to 5 μg/ml for 24 hr. Apoptosis is examined by evaluating Annexin V assay.

Example 9

Cannabinoids Effect on the Survival of Cancer Cells Harboring a NOTCH 2 Gain of Function Mutation The effects of cannabinoids on the survival of cancer cells harboring a NOTCH 2 gain of function mutation are examined. Prostate (PC3) and pancreas carcinoma (PANC1) cancer cells are exposed to *cannabis* extracts, CBD or CF1 single cannabinoids or combinations thereof at concentrations of 0.5 μg/ml to 5 μg/ml for 24 hr. Apoptosis is examined by evaluating Annexin V expression. In addition, protein is extracted from the cells and western blot analysis for NOTCH 2 intracellular domain (N2ICD) and its downstream signaling cyclooxygenase-2 (COX-2) is used to evaluate the effect of cannabinoids on NOTCH 2 signaling.

Example 10

Cannabinoids Effect on the Survival of Cancer Cells Harboring a NOTCH 3 Gain of Function Mutation The effects of cannabinoids on the survival of cancer cells harboring a NOTCH 3 gain of function mutation are examined. Non-small-cell lung cancer cells (NCIH460) harboring a NOTCH 3 gain of function mutation are exposed to *cannabis* extract, CBD or CF1 single cannabinoids or combinations thereof at concentrations of 0.5 μg/ml to 5 μg/ml for 24 hr. Apoptosis is examined by evaluating Annexin V expression. In addition, protein is extracted from the cells and western blot analysis for NOTCH 3 intracellular domain (N3ICD) and it downstream signaling HES1 and HEYL is used to evaluate the effect of cannabinoids on NOTCH 3 signaling.

Example 11

Cannabinoids Effect on Psoriasis Model

The efficacy of CBD and CF1 in the treatment of psoriasis is examined. Aldara (5% imiquimod)-induced acute skin inflammation model in mice is used (Horváth, et al. Sci Rep 9, 3685 (2019); and Wang et al. Hindawi Mediators of inflammation vol. 2020, Article ID 8297134). Mice are smeared with 62.5 mg of 5% imiquimod cream on shaved backs for 6 days and are administered with *Cannabis* extract CAN12 or CBD and CF1 at concentrations of 1 mg/kg to 50 mg/kg body weight via intraperitoneal (IP) injection.

Skin structural characters are observed daily, and the severity of psoriasis-like skin inflammation is evaluated by the target lesion score based on the clinical psoriasis area and severity index (PASI), except that the affected skin area is not taken into account in the overall score (van der Fits et al. Journal of Immunology. 2009; 182(9):5836-5845. doi: 10.4049/jimmunol.0802999.) Erythema, scaling, and thickening is scored independently on a scale of 0 to 4: 0, none; 1, slight; 2, moderate; 3, marked; and 4, very marked. The cumulative score (erythema plus scaling plus thickening) serves as a measure of the severity of inflammation (scale 0-12). After 6 consecutive days, all mice are anesthetized and blood is collected by heart puncture. Spleen and skin tissues are also collected for subsequent analysis.

Spleen cells from the model mice treated with cannabinoids and control are isolated and plated on a 24-well flat plate, each well containing in $1\times10^6$ cells, and polarized under the following conditions to generate IL-17A+γδ-FT Cell. Isolated splenic cells are grown in a medium of 5 μg/ml CD3 monoclonal antibody (mAb), 10 μg/ml CD28 mAb, 50 ng/ml recombinant IL-(rIL-) 1β, 50 ng/ml rIL-23, 50 ng/ml rIL-6, and 1 ng/ml TGF-β for 24 hr. IL17A cytokine is measured by ELISA.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of treating a subject afflicted with a disease related to any one of: NOTCH2, NOTCH3, NOTCH4, and combinations thereof, the method comprising administering to said subject a therapeutically effective amount of a pharmaceutical composition comprising as an active ingredient a cannabinoid referred to as CF1 having the following chemical structure:

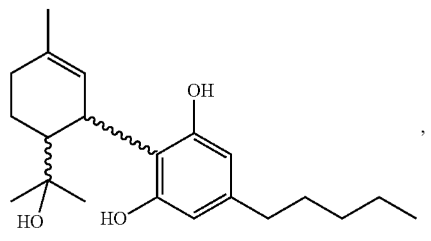 [SMILES: CCCCCc1cc(O)c(C2C=C(C)CCC2C(C)(C)O)c(O)c1]

, and a pharmaceutically acceptable carrier.

2. The method of claim 1, wherein the disease is characterized by an abnormal expression level of NOTCH2, NOTCH3, and/or NOTCH4.

3. The method of claim 1, wherein the disease is selected from the group consisting of: chronic inflammatory disease, rheumatoid arthritis, type 2 diabetes, psoriasis, glomerulosclerosis, cardiac disease, atherosclerosis, Alagille syndrome, Hajdu-Cheney syndrome, and cerebral autosomal dominant arteriopathy with subcortical infarcts and leukoencephalopathy (CADASIL) disorder.

4. The method of claim 1, wherein the pharmaceutical composition comprises CF1 as the sole cannabinoid.

5. The method of claim 1, wherein the pharmaceutical composition further comprises at least one additional cannabinoid.

6. The method of claim 1, wherein the pharmaceutical composition further comprises cannabidiol (CBD), cannabidivarin (CBDV), or both.

7. The method of claim 6, wherein CF1 and at least one of CBD and CBDV constitute more than 50% by weight of the cannabinoids in the pharmaceutical composition.

8. The method of claim 6, wherein the pharmaceutical composition comprises CF1, CBD, and CBDV.

9. The method of claim 8, wherein CF1, CBD, and CBDV constitute more than 50% by weight of the cannabinoids in the pharmaceutical composition.

10. The method of claim 6, wherein one or more of the cannabinoids is present as a highly purified extract of *Cannabis.*

11. The method of claim 6, wherein one or more of the cannabinoids is a synthetically produced cannabinoid.

* * * * *